(12) United States Patent
Byler

(10) Patent No.: US 10,817,004 B2
(45) Date of Patent: *Oct. 27, 2020

(54) VALVE SYSTEM WITH A PRESSURE SENSING DISPLACEMENT MEMBER

(71) Applicant: Fresenius Medical Care Holdings, Inc., Waltham, MA (US)

(72) Inventor: Terry Lynn Byler, Murrieta, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 7 days.

This patent is subject to a terminal disclaimer.

(21) Appl. No.: 16/003,814

(22) Filed: Jun. 8, 2018

(65) Prior Publication Data

US 2019/0138037 A1 May 9, 2019

Related U.S. Application Data

(63) Continuation of application No. 15/139,144, filed on Apr. 26, 2016, now Pat. No. 10,019,020, which is a
(Continued)

(51) Int. Cl.
*G05D 16/20* (2006.01)
*F16K 31/04* (2006.01)
(Continued)

(52) U.S. Cl.
CPC ............. *G05D 16/202* (2013.01); *A61M 1/14* (2013.01); *A61M 39/22* (2013.01); *F16K 31/04* (2013.01);
(Continued)

(58) Field of Classification Search
CPC .. A61M 1/14; A61M 39/22; A61M 2039/226; A61M 2205/10;
(Continued)

(56) References Cited

U.S. PATENT DOCUMENTS 2,276,843 A 3/1942 Hathaway
2,328,381 A * 8/1943 Jaffe ....................... E03C 1/086
285/8
(Continued)

FOREIGN PATENT DOCUMENTS

CN 2183771 Y 11/1994
CN 1146728 4/1997
(Continued)

OTHER PUBLICATIONS

Timby et al., Introductory Medical-Surgical Nursing, Lippincott Williams Wilkins, Ninth Edition, Chapter 28, p. 433.
(Continued)

*Primary Examiner* — David Colon-Morales
(74) *Attorney, Agent, or Firm* — Novel IP

(57) ABSTRACT

A system and method of monitoring and controlling the open and close states of a manifold diaphragm type valve includes using an actuator mechanism with feedback control. A pressure transducer and/or force gauge located on the contact end of the actuator mechanism monitors the pressure and/or force applied to the end of the actuator mechanism. A controller instructs the actuator mechanism to move forward or backward an appropriate distance based on the monitored pressure and/or force. Temperature and pressure changes in the system and material changes to the diaphragm are sensed immediately and positioning correction is applied to the actuator in real-time, thereby maintaining the same valve state while monitoring pressure separately. The linear actuator functions as a 'smart' actuator, capable of fine tune adjustments without additional outside monitoring and providing a more accurate and reliable method of closing the valve in a dynamic environment.

15 Claims, 9 Drawing Sheets

Related U.S. Application Data continuation of application No. 14/077,112, filed on Nov. 11, 2013, now Pat. No. 9,354,640.

(51) Int. Cl.
*A61M 1/14* (2006.01)
*A61M 39/22* (2006.01)
*F16K 37/00* (2006.01)

(52) U.S. Cl.
CPC ... *F16K 37/0083* (2013.01); *A61M 2039/226* (2013.01); *A61M 2205/10* (2013.01); *A61M 2205/128* (2013.01); *A61M 2205/332* (2013.01); *A61M 2205/3331* (2013.01); *Y10T 137/7761* (2015.04)

(58) Field of Classification Search
CPC ...... A61M 2205/128; A61M 2205/332; A61M 2205/3331; F16K 31/04; F16K 37/0083; F16K 31/046; F16K 7/04; F16K 7/045; G05D 16/202; G05D 16/02; G05D 16/10; G05D 3/12; G05D 3/127; G05D 3/1463; G05D 3/1481; G05D 3/183; G05D 3/20; G05D 3/203; G05D 15/01; G05D 7/0635; Y10T 137/7761; Y10T 137/8242
USPC .... 251/129.11, 129.12, 129.13, 4, 7, 8, 331, 251/335.2, 129.04
See application file for complete search history.

(56) References Cited

U.S. PATENT DOCUMENTS

| | | | |
|---|---|---|---|
| 2,569,105 A | 9/1951 | James | |
| 2,977,791 A | 4/1961 | Dubsky | |
| 3,200,591 A | 8/1965 | Ray | |
| 3,216,281 A | 11/1965 | Teichert | |
| 3,242,456 A * | 3/1966 | Duncan | H01R 13/02 439/252 |
| 3,308,798 A | 3/1967 | Snider | |
| 3,388,803 A * | 6/1968 | Scott | B01D 61/28 210/321.78 |
| 3,420,492 A * | 1/1969 | Ray | F16K 31/082 251/68 |
| 3,464,448 A | 9/1969 | Schmitz | |
| 3,511,469 A * | 5/1970 | Bell | F16K 7/045 251/7 |
| 3,514,674 A | 5/1970 | Ito Toshio | |
| 3,597,124 A | 8/1971 | Adams | |
| 3,669,878 A | 6/1972 | Marantz | |
| 3,669,880 A | 6/1972 | Marantz | |
| 3,709,222 A * | 1/1973 | DeVries | A61M 1/28 604/28 |
| 3,728,654 A | 4/1973 | Tada | |
| 3,746,175 A * | 7/1973 | Markley | B01D 61/28 210/321.64 |
| 3,752,189 A | 8/1973 | Marr | |
| 3,803,913 A * | 4/1974 | Tracer | G01F 1/68 73/204.14 |
| 3,814,376 A * | 6/1974 | Reinicke | F16K 31/082 251/65 |
| 3,841,799 A | 10/1974 | Spinosa | |
| 3,850,835 A | 11/1974 | Marantz | |
| 3,884,808 A * | 5/1975 | Scott | A61M 1/1696 210/109 |
| 3,894,431 A * | 7/1975 | Muston | G01F 1/667 73/861.29 |
| 3,902,490 A * | 9/1975 | Jacobsen | A61M 1/1696 210/321.65 |
| 3,918,037 A * | 11/1975 | Hall | G01G 19/16 340/626 |
| 3,927,955 A | 12/1975 | Spinosa | |
| 3,946,731 A * | 3/1976 | Lichtenstein | A61M 1/16 604/66 |
| 3,961,918 A * | 6/1976 | Johnson | B01D 19/0031 96/165 |
| 3,983,361 A | 9/1976 | Wild | |
| 3,989,622 A * | 11/1976 | Marantz | A61M 1/1696 210/645 |
| 3,989,625 A * | 11/1976 | Mason | A61M 1/3624 210/94 |
| 3,994,799 A * | 11/1976 | Yao | A61F 2/00 604/5.04 |
| 4,000,072 A * | 12/1976 | Sato | A61M 1/1696 210/315 |
| 4,047,099 A | 9/1977 | Berger | |
| 4,071,444 A * | 1/1978 | Ash | A61M 1/1696 210/232 |
| 4,079,007 A | 3/1978 | Hutchisson | |
| 4,083,777 A * | 4/1978 | Hutchisson | A61M 1/16 210/186 |
| 4,094,775 A * | 6/1978 | Mueller | A61M 1/1696 210/321.64 |
| 4,099,700 A * | 7/1978 | Young | F16K 7/16 251/129.11 |
| 4,113,614 A * | 9/1978 | Rollo | A61M 1/16 210/321.65 |
| 4,118,314 A * | 10/1978 | Yoshida | A61M 1/1696 210/140 |
| 4,155,852 A | 5/1979 | Fischel | |
| 4,159,748 A | 7/1979 | Staudinger | |
| 4,187,057 A | 2/1980 | Xanthopoulos | |
| 4,209,392 A * | 6/1980 | Wallace | A61M 1/1696 128/DIG. 3 |
| 4,212,738 A * | 7/1980 | Henne | A61M 1/1696 210/321.75 |
| 4,247,393 A * | 1/1981 | Wallace | A61M 1/3679 210/321.75 |
| 4,253,493 A | 3/1981 | English | |
| 4,259,985 A * | 4/1981 | Bergmann | F16K 7/045 137/595 |
| 4,267,040 A * | 5/1981 | Schal | A61M 1/16 210/104 |
| 4,269,708 A * | 5/1981 | Bonomini | A61M 1/1696 210/103 |
| 4,326,955 A * | 4/1982 | Babb | C01D 7/10 210/638 |
| 4,348,283 A * | 9/1982 | Ash | A61M 1/267 210/321.67 |
| 4,354,562 A * | 10/1982 | Newman | G01G 7/00 177/210 EM |
| 4,368,737 A * | 1/1983 | Ash | A61M 1/285 604/175 |
| 4,371,385 A | 2/1983 | Johnson | |
| 4,381,999 A | 5/1983 | Boucher | |
| 4,387,777 A * | 6/1983 | Ash | G01G 19/40 177/1 |
| 4,390,073 A | 6/1983 | Rosen | |
| 4,397,189 A * | 8/1983 | Johnson | G01F 1/007 73/223 |
| 4,397,519 A * | 8/1983 | Cooney | H01R 13/2421 324/755.05 |
| 4,402,694 A * | 9/1983 | Ash | A61F 2/022 424/424 |
| 4,403,765 A * | 9/1983 | Fisher | F16K 31/082 137/625.65 |
| 4,403,984 A * | 9/1983 | Ash | A61B 5/14528 600/364 |
| 4,413,988 A * | 11/1983 | Handt | A61M 1/28 604/131 |
| 4,430,098 A * | 2/1984 | Bowman | B01D 19/0031 210/188 |
| 4,436,620 A | 3/1984 | Bellotti | |
| 4,443,333 A * | 4/1984 | Mahurkar | A61M 1/16 210/321.65 |
| 4,460,555 A | 7/1984 | Thompson | |
| 4,464,172 A * | 8/1984 | Lichtenstein | A61B 5/00 604/65 |
| 4,466,804 A * | 8/1984 | Hino | A61M 1/3621 128/DIG. 3 |

(56) References Cited

U.S. PATENT DOCUMENTS

| | | | | |
|---|---|---|---|---|
| 4,469,593 A * | 9/1984 | Ishihara | A61M 1/16 | 210/104 |
| 4,477,342 A * | 10/1984 | Allan | A61M 1/16 | 210/321.71 |
| 4,480,483 A * | 11/1984 | McShane | G01F 1/661 | 73/861.27 |
| 4,498,902 A * | 2/1985 | Ash | A61M 25/0668 | 600/585 |
| 4,531,799 A * | 7/1985 | Gray | G01R 1/073 | 439/298 |
| 4,535,637 A * | 8/1985 | Feller | G01F 1/10 | 73/861.77 |
| 4,559,039 A * | 12/1985 | Ash | A61M 5/1582 | 604/175 |
| 4,563,170 A * | 1/1986 | Aigner | A61M 1/34 | 604/27 |
| 4,581,141 A * | 4/1986 | Ash | A61M 1/1696 | 210/321.84 |
| 4,586,576 A | 5/1986 | Inoue | | |
| 4,596,550 A * | 6/1986 | Troutner | A61M 1/30 | 128/DIG. 13 |
| 4,599,055 A * | 7/1986 | Dykstra | F04B 43/1284 | 417/477.11 |
| 4,606,826 A * | 8/1986 | Sano | A61M 1/16 | 210/136 |
| 4,630,799 A * | 12/1986 | Nolan | F16K 31/082 | 137/460 |
| 4,650,587 A | 3/1987 | Polak | | |
| 4,661,246 A * | 4/1987 | Ash | A61M 1/1696 | 210/110 |
| 4,666,598 A * | 5/1987 | Heath | A61M 1/3621 | 210/137 |
| 4,680,122 A * | 7/1987 | Barone | A61M 1/1694 | 210/321.6 |
| 4,683,053 A * | 7/1987 | Polaschegg | A61M 1/169 | 210/321.6 |
| 4,710,164 A * | 12/1987 | Levin | A61M 1/16 | 210/646 |
| 4,731,072 A | 3/1988 | Aid | | |
| 4,740,755 A * | 4/1988 | Ogawa | G01N 27/023 | 324/442 |
| 4,750,705 A * | 6/1988 | Zippe | F16K 31/003 | 137/248 |
| 4,762,618 A * | 8/1988 | Gummesson | A61M 1/16 | 210/110 |
| 4,765,421 A | 8/1988 | Newton | | |
| 4,765,907 A * | 8/1988 | Scott | A61M 1/1696 | 210/321.78 |
| 4,777,953 A * | 10/1988 | Ash | A61B 5/14528 | 600/347 |
| 4,802,540 A | 2/1989 | Grabovac | | |
| 4,806,247 A * | 2/1989 | Schoendorfer | A61M 1/30 | 210/321.68 |
| 4,808,089 A | 2/1989 | Buchholtz | | |
| 4,815,547 A | 3/1989 | Dillon | | |
| 4,823,597 A | 4/1989 | White | | |
| 4,826,663 A | 5/1989 | Alberti | | |
| 4,828,543 A * | 5/1989 | Weiss | A61M 1/16 | 210/637 |
| 4,828,693 A | 5/1989 | Lindsay | | |
| 4,831,884 A * | 5/1989 | Drenthen | G01F 1/662 | 73/861.27 |
| 4,840,542 A * | 6/1989 | Abbott | A61M 5/14224 | 417/28 |
| 4,854,322 A * | 8/1989 | Ash | A61B 5/14528 | 600/347 |
| 4,861,242 A * | 8/1989 | Finsterwald | F04B 43/1253 | 417/477.2 |
| 4,881,839 A | 11/1989 | Grimm | | |
| 4,882,937 A | 11/1989 | Leon | | |
| 4,885,942 A * | 12/1989 | Magori | G01F 1/667 | 73/861.28 |
| 4,894,164 A | 1/1990 | Polaschegg | | |
| 4,897,189 A * | 1/1990 | Greenwood | A61M 1/30 | 210/195.2 |
| 4,909,713 A * | 3/1990 | Finsterwald | F04B 43/1253 | 417/477.1 |
| 4,914,819 A * | 4/1990 | Ash | A47G 21/02 | 30/141 |
| 4,931,777 A | 6/1990 | Chiang | | |
| 4,943,279 A * | 7/1990 | Samiotes | A61M 5/1456 | 604/151 |
| 4,950,244 A * | 8/1990 | Fellingham | A61M 5/16854 | 600/488 |
| 4,950,395 A * | 8/1990 | Richalley | A61M 1/16 | 210/195.2 |
| 4,968,422 A * | 11/1990 | Runge | A61M 1/3621 | 210/321.69 |
| 4,985,015 A | 1/1991 | Obermann | | |
| 4,990,258 A * | 2/1991 | Bjare | A61M 1/16 | 210/647 |
| 4,994,035 A * | 2/1991 | Mokros | A61B 5/02152 | 200/83 J |
| 4,995,268 A * | 2/1991 | Ash | A61M 1/3663 | 210/647 |
| 4,997,570 A * | 3/1991 | Polaschegg | A61M 1/16 | 210/123 |
| 5,000,274 A | 3/1991 | Bullivant | | |
| 5,002,054 A * | 3/1991 | Ash | A61B 5/14528 | 600/347 |
| 5,009,101 A * | 4/1991 | Branam | F16K 31/046 | 73/168 |
| 5,011,607 A * | 4/1991 | Shinzato | A61M 1/16 | 210/110 |
| 5,024,586 A | 6/1991 | Meiri | | |
| 5,032,261 A * | 7/1991 | Pyper | B01D 24/04 | 210/137 |
| 5,074,368 A * | 12/1991 | Bullivant | G07G 1/0054 | 177/185 |
| 5,100,554 A * | 3/1992 | Polaschegg | A61M 1/16 | 210/646 |
| 5,114,580 A * | 5/1992 | Ahmad | A61M 1/1684 | 210/143 |
| 5,138,138 A | 8/1992 | Theilacker | | |
| 5,147,613 A * | 9/1992 | Heilmann | A61L 2/04 | 134/102.1 |
| 5,152,174 A * | 10/1992 | LaBudde | G01F 1/667 | 73/861.02 |
| 5,157,332 A * | 10/1992 | Reese | G01N 27/023 | 324/204 |
| 5,161,779 A * | 11/1992 | Graner | H01F 7/1646 | 251/129.16 |
| 5,170,789 A * | 12/1992 | Narayan | A61B 1/00142 | 324/318 |
| 5,188,604 A * | 2/1993 | Orth | A61M 1/10 | 128/DIG. 13 |
| 5,198,335 A * | 3/1993 | Sekikawa | C12Q 1/32 | 422/417 |
| 5,211,643 A * | 5/1993 | Reinhardt | A61M 1/287 | 206/221 |
| 5,215,450 A * | 6/1993 | Tamari | A61M 1/0031 | 138/119 |
| 5,220,843 A * | 6/1993 | Rak | G01L 5/0061 | 251/129.04 |
| 5,228,308 A * | 7/1993 | Day | F25B 5/04 | 62/198 |
| 5,230,341 A * | 7/1993 | Polaschegg | A61M 1/16 | 600/481 |
| 5,230,614 A * | 7/1993 | Zanger | F04B 43/1284 | 417/477.9 |
| 5,258,127 A * | 11/1993 | Gsell | A61M 1/3633 | 210/188 |
| 5,259,961 A | 11/1993 | Eigendorf | | |
| 5,277,820 A * | 1/1994 | Ash | A61M 1/3458 | 210/117 |
| 5,284,470 A * | 2/1994 | Beltz | A61M 1/3472 | 210/321.71 |

(56) References Cited

U.S. PATENT DOCUMENTS

| | | | |
|---|---|---|---|
| 5,284,559 A * | 2/1994 | Lim | B01D 57/02 204/461 |
| 5,295,505 A * | 3/1994 | Polaschegg | A61M 1/1656 137/93 |
| 5,304,114 A | 4/1994 | Cosman | |
| 5,304,349 A * | 4/1994 | Polaschegg | A61M 1/169 422/105 |
| 5,308,315 A * | 5/1994 | Khuri | A61M 1/16 210/646 |
| 5,322,258 A * | 6/1994 | Bosch | F15C 5/00 251/129.01 |
| 5,322,519 A * | 6/1994 | Ash | A61M 1/284 604/264 |
| 5,336,165 A | 8/1994 | Twardowski | |
| 5,339,699 A | 8/1994 | Carignan | |
| 5,346,472 A * | 9/1994 | Keshaviah | A61M 1/1605 604/65 |
| 5,347,115 A | 9/1994 | Sherman | |
| 5,352,364 A | 10/1994 | Kruger | |
| 5,360,445 A * | 11/1994 | Goldowsky | A61M 1/106 600/16 |
| 5,385,005 A * | 1/1995 | Ash | A01D 34/84 56/12.7 |
| D355,816 S * | 2/1995 | Ash | D8/1 |
| 5,391,143 A * | 2/1995 | Kensey | A61M 27/002 604/28 |
| 5,405,315 A | 4/1995 | Khuri | |
| 5,405,320 A * | 4/1995 | Twardowski | A61M 5/1582 604/264 |
| 5,408,576 A | 4/1995 | Bishop | |
| 5,415,532 A * | 5/1995 | Loughnane | F04B 43/082 417/411 |
| 5,441,636 A * | 8/1995 | Chevallet | A61M 1/16 210/232 |
| 5,445,630 A * | 8/1995 | Richmond | A61M 5/162 604/403 |
| 5,460,493 A * | 10/1995 | Deniega | A61M 1/3621 417/475 |
| 5,468,388 A | 11/1995 | Goddard | |
| 5,469,737 A * | 11/1995 | Smith | G01L 5/0061 73/168 |
| 5,476,444 A * | 12/1995 | Keeling | A61F 7/08 604/6.13 |
| 5,518,015 A * | 5/1996 | Berget | F16K 31/04 137/1 |
| D370,531 S * | 6/1996 | Ash | D24/112 |
| 5,536,412 A * | 7/1996 | Ash | A61M 1/1696 210/195.1 |
| 5,540,265 A * | 7/1996 | Polaschegg | A61M 1/1656 141/114 |
| 5,545,131 A * | 8/1996 | Davankov | A61M 1/3679 210/646 |
| 5,577,891 A * | 11/1996 | Loughnane | F04B 43/082 417/412 |
| 5,580,460 A * | 12/1996 | Polaschegg | A61M 1/16 210/138 |
| 5,591,344 A | 1/1997 | Kenley | |
| 5,609,770 A * | 3/1997 | Zimmerman | A61M 1/16 210/739 |
| 5,614,677 A * | 3/1997 | Wamsiedler | A61M 1/3639 318/568.19 |
| 5,616,305 A * | 4/1997 | Mathieu | A61M 1/1656 206/568 |
| 5,624,551 A * | 4/1997 | Baumann | A61M 1/169 137/456 |
| 5,624,572 A | 4/1997 | Larson | |
| 5,629,871 A * | 5/1997 | Love | A61M 1/16 702/34 |
| 5,632,897 A * | 5/1997 | Mathieu | A61K 31/194 210/645 |
| 5,644,285 A * | 7/1997 | Maurer | G01L 9/0052 338/39 |
| 5,647,853 A * | 7/1997 | Feldmann | A61M 5/16854 604/131 |
| 5,650,704 A | 7/1997 | Pratt | |
| 5,674,390 A * | 10/1997 | Matthews | A61L 2/04 210/261 |
| 5,679,245 A * | 10/1997 | Manica | A61M 1/16 210/134 |
| 5,685,835 A | 11/1997 | Brugger | |
| 5,690,821 A | 11/1997 | Kenley | |
| 5,693,008 A * | 12/1997 | Brugger | A61M 1/3639 600/485 |
| 5,695,473 A * | 12/1997 | Olsen | A61M 5/16859 604/153 |
| 5,698,083 A * | 12/1997 | Glass | C12Q 1/58 204/403.03 |
| 5,711,883 A * | 1/1998 | Folden | A61M 1/16 210/646 |
| 5,713,850 A * | 2/1998 | Heilmann | A61M 1/285 137/625.46 |
| 5,725,773 A * | 3/1998 | Polaschegg | A61M 1/16 134/166 R |
| 5,725,776 A | 3/1998 | Kenley | |
| 5,744,027 A * | 4/1998 | Connell | A61M 1/16 210/96.2 |
| 5,760,313 A * | 6/1998 | Guentner | G01L 1/18 73/862.584 |
| 5,762,782 A | 6/1998 | Kenley | |
| 5,765,591 A * | 6/1998 | Wasson | B01J 19/0046 137/597 |
| 5,770,806 A * | 6/1998 | Hiismaki | G01F 1/662 73/861.18 |
| 5,782,796 A * | 7/1998 | Din | A61M 1/28 604/27 |
| 5,794,669 A | 8/1998 | Polaschegg | |
| 5,840,068 A * | 11/1998 | Cartledge | A61M 5/142 604/131 |
| 5,858,186 A * | 1/1999 | Glass | C12Q 1/005 204/403.14 |
| 5,876,419 A * | 3/1999 | Carpenter | A61F 2/915 606/198 |
| 5,902,336 A * | 5/1999 | Mishkin | A61F 2/064 604/27 |
| 5,906,978 A * | 5/1999 | Ash | A61K 33/26 424/648 |
| 5,919,369 A * | 7/1999 | Ash | A61M 1/3472 210/195.1 |
| 5,928,177 A * | 7/1999 | Brugger | A61M 1/10 604/6.11 |
| 5,938,938 A * | 8/1999 | Bosetto | A61M 1/16 210/739 |
| 5,944,684 A * | 8/1999 | Roberts | A61M 1/1696 210/646 |
| 5,945,343 A * | 8/1999 | Munkholm | C12Q 1/58 422/420 |
| 5,947,953 A * | 9/1999 | Ash | A61M 25/0021 138/115 |
| 5,951,870 A * | 9/1999 | Utterberg | A61M 1/3647 210/188 |
| 5,980,481 A * | 11/1999 | Gorsuch | A61M 1/1678 604/28 |
| 5,984,891 A * | 11/1999 | Keilman | A61M 1/28 604/65 |
| 5,989,423 A * | 11/1999 | Kamen | A61M 1/28 210/180 |
| 5,989,438 A * | 11/1999 | Fumiyama | A61M 1/36 210/745 |
| 6,012,342 A | 1/2000 | Blight | |
| 6,042,561 A * | 3/2000 | Ash | A61M 39/0247 604/93.01 |
| 6,044,691 A * | 4/2000 | Kenley | A61M 1/3621 210/646 |
| 6,047,108 A | 4/2000 | Sword | |
| 6,062,256 A | 5/2000 | Miller | |
| 6,069,343 A | 5/2000 | Kolowich | |
| 6,086,753 A * | 7/2000 | Ericson | A61M 1/1658 137/88 |

(56) References Cited

U.S. PATENT DOCUMENTS

| | | | |
|---|---|---|---|
| 6,116,269 A | 9/2000 | Maxson | |
| 6,117,100 A * | 9/2000 | Powers | A61M 1/16 210/645 |
| 6,117,122 A | 9/2000 | Din | |
| 6,118,082 A | 9/2000 | Bissette | |
| 6,121,555 A | 9/2000 | Nowosielski | |
| 6,156,007 A * | 12/2000 | Ash | A61M 1/3679 604/113 |
| 6,168,578 B1 * | 1/2001 | Diamond | A61M 1/28 2/312 |
| 6,187,199 B1 | 2/2001 | Goldau | |
| 6,190,349 B1 | 2/2001 | Ash | |
| 6,196,922 B1 * | 3/2001 | Hantschk | F16D 3/185 464/159 |
| 6,200,485 B1 * | 3/2001 | Kitaevich | A61M 1/16 210/134 |
| 6,217,540 B1 * | 4/2001 | Yazawa | G01N 33/491 604/4.01 |
| 6,228,047 B1 | 5/2001 | Dadson | |
| 6,234,989 B1 * | 5/2001 | Brierton | A61M 1/3624 604/5.01 |
| 6,240,789 B1 | 6/2001 | Morlan | |
| 6,254,567 B1 * | 7/2001 | Treu | A61M 1/1696 604/29 |
| 6,264,611 B1 * | 7/2001 | Ishikawa | A61B 5/0031 600/485 |
| 6,264,680 B1 * | 7/2001 | Ash | A61M 1/3621 604/6.13 |
| 6,280,406 B1 * | 8/2001 | Dolecek | A61M 1/3624 210/645 |
| 6,284,131 B1 | 9/2001 | Hogard | |
| 6,287,516 B1 * | 9/2001 | Matson | A61M 1/3472 210/650 |
| 6,289,749 B1 | 9/2001 | Sanders | |
| 6,303,036 B1 * | 10/2001 | Collins | A61M 1/342 210/143 |
| 6,325,774 B1 * | 12/2001 | Bene | A61M 1/16 210/321.71 |
| 6,332,985 B1 * | 12/2001 | Sherman | A61M 1/28 210/638 |
| 6,341,758 B1 | 1/2002 | Shih | |
| 6,348,162 B1 | 2/2002 | Ash | |
| 6,354,565 B1 | 3/2002 | Doust | |
| 6,406,631 B1 * | 6/2002 | Collins | A61M 1/3413 210/143 |
| 6,409,699 B1 * | 6/2002 | Ash | A61M 1/1696 604/29 |
| 6,416,293 B1 * | 7/2002 | Bouchard | A61M 1/367 137/599.14 |
| 6,468,427 B1 * | 10/2002 | Frey | A61M 1/3627 210/497.01 |
| 6,471,872 B2 | 10/2002 | Kitaevich | |
| 6,487,904 B1 * | 12/2002 | Myhre | G01F 1/684 73/204.12 |
| 6,491,656 B1 * | 12/2002 | Morris | A61M 1/3621 210/257.2 |
| 6,491,673 B1 * | 12/2002 | Palumbo | A61F 13/82 604/317 |
| 6,497,675 B1 * | 12/2002 | Davankov | A61M 1/3472 210/433.1 |
| 6,517,044 B1 | 2/2003 | Lin | |
| 6,517,045 B1 * | 2/2003 | Northedge | F16K 31/082 251/129.16 |
| 6,551,513 B2 * | 4/2003 | Nikaido | A61M 1/3643 210/321.69 |
| 6,554,789 B1 * | 4/2003 | Brugger | A61M 1/34 210/252 |
| 6,561,997 B1 * | 5/2003 | Weitzel | A61M 1/16 210/645 |
| 6,565,395 B1 * | 5/2003 | Schwarz | G01C 19/5691 439/816 |
| 6,572,576 B2 * | 6/2003 | Brugger | A61M 1/3626 210/646 |
| 6,572,641 B2 * | 6/2003 | Brugger | A61F 7/0085 607/106 |
| 6,579,253 B1 * | 6/2003 | Burbank | A61M 1/34 210/252 |
| 6,579,460 B1 * | 6/2003 | Willis | B01J 39/02 210/483 |
| 6,582,385 B2 * | 6/2003 | Burbank | A61M 1/3472 210/646 |
| 6,589,482 B1 | 7/2003 | Burbank | |
| 6,595,943 B1 * | 7/2003 | Burbank | A61M 1/34 210/257.2 |
| 6,607,495 B1 * | 8/2003 | Skalak | A61B 5/411 600/573 |
| 6,610,036 B2 * | 8/2003 | Branch | B65D 35/28 604/295 |
| 6,623,470 B2 * | 9/2003 | Munis | A61B 5/021 600/485 |
| 6,627,164 B1 * | 9/2003 | Wong | A61M 1/1696 423/420.2 |
| 6,632,192 B2 * | 10/2003 | Gorsuch | A61M 1/1678 604/6.04 |
| 6,638,477 B1 * | 10/2003 | Treu | A61M 1/34 210/252 |
| 6,638,478 B1 * | 10/2003 | Treu | A61M 1/34 210/252 |
| 6,649,063 B2 * | 11/2003 | Brugger | A61M 1/3462 210/645 |
| 6,653,841 B1 * | 11/2003 | Koerdt | G01N 27/023 324/445 |
| 6,673,314 B1 * | 1/2004 | Burbank | A61M 1/34 128/898 |
| 6,681,624 B2 * | 1/2004 | Furuki | G01F 1/696 73/204.13 |
| 6,685,664 B2 * | 2/2004 | Levin | A61M 1/34 210/321.6 |
| 6,690,280 B2 * | 2/2004 | Citrenbaum | A61M 5/16895 128/DIG. 13 |
| 6,695,803 B1 * | 2/2004 | Robinson | A61M 1/02 210/252 |
| 6,702,561 B2 * | 3/2004 | Stillig | B01D 63/022 210/321.8 |
| 6,706,007 B2 * | 3/2004 | Gelfand | A61M 1/34 604/4.01 |
| 6,730,266 B2 | 5/2004 | Matson | |
| 6,743,193 B2 * | 6/2004 | Brugger | A61M 1/367 137/625.43 |
| 6,752,172 B2 * | 6/2004 | Lauer | A61M 1/367 137/605 |
| 6,758,975 B2 * | 7/2004 | Peabody | A61L 2/022 210/257.2 |
| 6,764,460 B2 | 7/2004 | Dolecek | |
| 6,773,412 B2 * | 8/2004 | O'Mahony | A61M 1/16 604/5.01 |
| 6,776,912 B2 * | 8/2004 | Baurmeister | A61M 1/3413 210/321.79 |
| 6,796,955 B2 * | 9/2004 | O'Mahony | A61M 1/3653 604/6.11 |
| 6,818,196 B2 | 11/2004 | Wong | |
| 6,830,553 B1 * | 12/2004 | Burbank | A61M 1/34 210/321.6 |
| 6,836,201 B1 * | 12/2004 | Devenyi | H01F 7/1816 335/229 |
| 6,841,172 B1 | 1/2005 | Ash | |
| 6,843,779 B1 * | 1/2005 | Andrysiak | A61M 1/34 210/195.2 |
| 6,852,090 B2 * | 2/2005 | Burbank | A61M 1/34 210/252 |
| 6,872,346 B2 * | 3/2005 | Stillig | B01D 63/021 264/261 |
| 6,878,283 B2 * | 4/2005 | Thompson | A61M 1/1696 210/232 |
| 6,886,801 B2 | 5/2005 | Mangus Hallb | |
| 6,890,315 B1 * | 5/2005 | Levin | A61M 1/34 210/645 |

(56) References Cited

U.S. PATENT DOCUMENTS

| | | | | |
|---|---|---|---|---|
| 6,899,691 B2* | 5/2005 | Bainbridge | ............. | A61M 1/30 604/4.01 |
| 6,923,782 B2 | 8/2005 | Omahony | | |
| 6,948,697 B2* | 9/2005 | Herbert | ............... | F16K 31/0672 251/129.04 |
| 6,955,655 B2* | 10/2005 | Burbank | ........... | A61M 39/0208 210/195.2 |
| 6,958,049 B1* | 10/2005 | Ash | ........................ | A61L 29/14 514/574 |
| 6,960,179 B2* | 11/2005 | Gura | ........................ | A61M 1/16 210/321.8 |
| 6,960,328 B2* | 11/2005 | Bortun | ..................... | B01J 27/16 210/681 |
| 6,979,309 B2* | 12/2005 | Burbank | ................ | A61M 1/282 604/6.16 |
| 7,004,924 B1* | 2/2006 | Brugger | .................. | A61M 1/3626 600/16 |
| 7,007,549 B2* | 3/2006 | Kwon | ........................ | G01F 1/69 73/204.14 |
| 7,033,498 B2* | 4/2006 | Wong | .................. | A61M 1/1696 210/264 |
| 7,037,428 B1 | 5/2006 | Robinson | | |
| 7,040,142 B2* | 5/2006 | Burbank | ................ | A61M 1/367 340/605 |
| 7,059,195 B1 | 6/2006 | Liu | | |
| 7,087,026 B2* | 8/2006 | Callister | ................ | A61B 5/029 600/504 |
| 7,087,033 B2 | 8/2006 | Brugger | | |
| 7,097,148 B2 | 8/2006 | DeWall | | |
| 7,101,519 B2 | 9/2006 | Wong | | |
| 7,112,273 B2* | 9/2006 | Weigel | ..................... | A61M 1/16 137/100 |
| 7,115,095 B2* | 10/2006 | Eigler | .................. | A61B 5/0215 600/486 |
| 7,135,156 B2* | 11/2006 | Hai | ........................ | C01G 25/02 423/69 |
| 7,144,386 B2* | 12/2006 | Korkor | ............. | A61M 25/0662 604/164.03 |
| 7,146,861 B1 | 12/2006 | Cook | | |
| 7,147,613 B2* | 12/2006 | Burbank | ................. | A61M 1/34 604/5.01 |
| 7,169,303 B2* | 1/2007 | Sullivan | ............... | A61M 1/1696 210/206 |
| 7,175,809 B2 | 2/2007 | Gelfand | | |
| 7,214,312 B2 | 5/2007 | Brugger | | |
| 7,226,538 B2* | 6/2007 | Brugger | ............. | A61M 1/3643 210/194 |
| 7,241,272 B2* | 7/2007 | Karoor | ................ | A61M 1/1696 604/5.01 |
| 7,252,767 B2* | 8/2007 | Bortun | ..................... | B01J 21/06 210/660 |
| 7,267,658 B2 | 9/2007 | Treu | | |
| 7,270,015 B1* | 9/2007 | Feller | .................... | G01F 1/7044 600/547 |
| 7,273,465 B2* | 9/2007 | Ash | ..................... | A61M 1/3621 210/739 |
| 7,276,042 B2* | 10/2007 | Polaschegg | ............ | B01D 61/00 210/500.21 |
| 7,300,413 B2 | 11/2007 | Burbank | | |
| 7,309,323 B2* | 12/2007 | Gura | ........................ | A61M 1/16 210/645 |
| 7,314,208 B1* | 1/2008 | Rightley | .................... | F16K 7/12 251/129.15 |
| 7,317,967 B2* | 1/2008 | DiGianfilippo | ......... | A61J 3/002 700/265 |
| 7,332,096 B2* | 2/2008 | Blickhan | ................ | A61M 1/3633 210/335 |
| 7,337,674 B2* | 3/2008 | Burbank | ............. | A61M 1/3639 73/714 |
| 7,338,460 B2 | 3/2008 | Burbank | | |
| 7,347,849 B2* | 3/2008 | Brugger | ................. | A61M 1/34 210/645 |
| 7,351,218 B2* | 4/2008 | Bene | .................... | A61M 1/342 210/739 |
| 7,387,022 B1* | 6/2008 | Korniyenko | .......... | G01F 1/6842 73/204.11 |
| 7,494,590 B2* | 2/2009 | Felding | .................... | A61M 1/16 210/646 |
| 7,531,098 B2* | 5/2009 | Robinson | ............ | A61M 1/3693 210/102 |
| 7,566,432 B2 | 7/2009 | Wong | | |
| 7,597,677 B2* | 10/2009 | Gura | ........................ | A61M 1/16 210/195.2 |
| 7,605,710 B2* | 10/2009 | Crnkovich | ............... | A61F 13/42 340/603 |
| 7,618,531 B2* | 11/2009 | Sugioka | .................. | A61M 1/16 210/85 |
| 7,628,378 B2* | 12/2009 | Adams | .................. | F16K 31/082 251/129.04 |
| 7,645,253 B2* | 1/2010 | Gura | ........................ | A61M 1/16 210/645 |
| 7,648,476 B2* | 1/2010 | Bock | ........................ | A61M 1/16 604/4.01 |
| 7,696,762 B2* | 4/2010 | Quackenbush | ...... | G01N 27/023 324/446 |
| 7,713,226 B2* | 5/2010 | Ash | ........................ | A61M 1/16 210/134 |
| 7,736,507 B2 | 6/2010 | Wong | | |
| 7,755,488 B2* | 7/2010 | Dvorsky | ............. | A61M 1/3656 340/572.1 |
| 7,766,873 B2* | 8/2010 | Moberg | ............ | A61M 5/16854 604/131 |
| 7,776,210 B2 | 8/2010 | Rosenbaum | | |
| 7,780,619 B2* | 8/2010 | Brugger | ............. | A61M 1/3441 210/252 |
| 7,794,141 B2* | 9/2010 | Perry | ..................... | A61M 1/369 374/44 |
| 7,861,740 B2* | 1/2011 | Phallen | .................... | F16K 7/045 137/487.5 |
| 7,873,489 B2* | 1/2011 | Dolgos | ................. | A61M 1/16 210/143 |
| 7,874,999 B2* | 1/2011 | Busby | ................. | A61M 1/3653 600/309 |
| 7,886,611 B2 | 2/2011 | OMahony | | |
| 7,896,829 B2 | 3/2011 | Gura | | |
| 7,901,376 B2* | 3/2011 | Steck | ....................... | A61M 1/28 604/131 |
| 7,914,477 B2 | 3/2011 | Briggs | | |
| 7,922,898 B2* | 4/2011 | Jonsson | ................. | A61M 1/367 137/597 |
| 7,922,899 B2* | 4/2011 | Vasta | ...................... | A61M 1/16 210/143 |
| 7,935,074 B2* | 5/2011 | Plahey | .................... | A61M 1/28 210/646 |
| 7,959,129 B2* | 6/2011 | Matsumoto | .......... | F16K 31/0655 251/129.15 |
| 7,981,082 B2 | 7/2011 | Wang | | |
| 7,981,280 B2* | 7/2011 | Carr | ....................... | A61M 1/16 210/134 |
| 7,995,816 B2 | 8/2011 | Roger | | |
| 7,998,101 B2 | 8/2011 | Ash | | |
| 8,021,319 B2 | 9/2011 | Delnevo | | |
| 8,029,454 B2 | 10/2011 | Kelly | | |
| 8,034,161 B2 | 10/2011 | Gura | | |
| 8,034,235 B2 | 10/2011 | Rohde | | |
| 8,062,513 B2 | 11/2011 | Yu | | |
| 8,066,658 B2 | 11/2011 | Karoor | | |
| 8,070,707 B2 | 12/2011 | Gelfand | | |
| 8,075,509 B2 | 12/2011 | Molducci | | |
| 8,078,333 B2 | 12/2011 | Kienman | | |
| 8,083,677 B2 | 12/2011 | Rohde | | |
| 8,105,260 B2 | 1/2012 | Tonelli | | |
| 8,105,487 B2 | 1/2012 | Fulkerson | | |
| 8,114,288 B2 | 2/2012 | Robinson | | |
| 8,118,276 B2 | 2/2012 | Sanders | | |
| 8,123,947 B2 | 2/2012 | Rohde | | |
| 8,152,751 B2 | 2/2012 | Roger | | |
| 8,142,383 B2 | 3/2012 | Dannenmaier | | |
| 8,187,184 B2 | 5/2012 | Muller | | |

(56) References Cited

U.S. PATENT DOCUMENTS

| | | | |
|---|---|---|---|
| 8,192,401 B2* | 6/2012 | Morris | A61M 1/14 604/153 |
| 8,197,431 B2 | 6/2012 | Bennison | |
| 8,206,338 B2* | 6/2012 | Childers | A61M 1/1696 604/29 |
| 8,210,493 B2* | 7/2012 | Miyagawa | F16K 31/046 251/285 |
| 8,221,320 B2 | 7/2012 | Bouton | |
| 8,240,636 B2* | 8/2012 | Smith | F16K 31/082 251/129.19 |
| 8,273,049 B2 | 9/2012 | Demers | |
| 8,316,725 B2* | 11/2012 | Wade | G01L 1/18 73/760 |
| 8,323,492 B2 | 12/2012 | Childers | |
| 8,342,478 B1 | 1/2013 | Cordray | |
| 8,376,978 B2 | 2/2013 | Roger | |
| 8,449,487 B2 | 5/2013 | Hovland | |
| 8,491,184 B2 | 7/2013 | Kamen | |
| 8,597,505 B2 | 12/2013 | Fulkerson | |
| 8,622,365 B2* | 1/2014 | Fukano | F16K 7/045 251/7 |
| 8,696,626 B2 | 4/2014 | Kirsch | |
| 9,308,307 B2 | 4/2016 | Fulkerson | |
| 9,354,640 B2* | 5/2016 | Byler | A61M 1/14 |
| 9,360,129 B2 | 6/2016 | Smith | |
| 9,517,296 B2 | 12/2016 | Fulkerson | |
| 1,001,902 A1 | 7/2018 | Byler | |
| 1,025,873 A1 | 4/2019 | Fulkerson | |
| 2001/0038083 A1* | 11/2001 | Sakurai | F16K 31/007 251/129.06 |
| 2002/0050412 A1 | 5/2002 | Emery | |
| 2002/0068364 A1 | 6/2002 | Arai | |
| 2002/0085951 A1 | 7/2002 | Gelfand | |
| 2002/0112609 A1 | 8/2002 | Wong | |
| 2002/0113016 A1 | 8/2002 | Takai | |
| 2002/0139419 A1* | 10/2002 | Flinchbaugh | A61M 25/04 137/557 |
| 2002/0147423 A1 | 10/2002 | Burbank | |
| 2002/0158019 A1 | 10/2002 | Collins | |
| 2002/0187069 A1 | 12/2002 | Levin | |
| 2002/0193679 A1 | 12/2002 | Malave | |
| 2003/0001590 A1* | 1/2003 | Mengle | G01D 5/24 324/662 |
| 2003/0012905 A1 | 1/2003 | Zumbrum | |
| 2003/0042181 A1 | 3/2003 | Metzner | |
| 2003/0048185 A1 | 3/2003 | Citrenbaum | |
| 2003/0056585 A1 | 3/2003 | Furuki | |
| 2003/0113931 A1 | 6/2003 | Pan | |
| 2003/0113932 A1 | 6/2003 | Sternberg | |
| 2003/0128125 A1 | 7/2003 | Burbank | |
| 2003/0216677 A1 | 11/2003 | Pan | |
| 2003/0220598 A1 | 11/2003 | Busby | |
| 2003/0220606 A1 | 11/2003 | Busby | |
| 2003/0236482 A1 | 12/2003 | Gorsuch | |
| 2004/0018100 A1* | 1/2004 | Takagi | F04B 43/046 417/322 |
| 2004/0019312 A1 | 1/2004 | Childers | |
| 2004/0021108 A1 | 2/2004 | Hallback | |
| 2004/0031756 A1 | 2/2004 | Suzuki | |
| 2004/0167465 A1 | 8/2004 | Mihai | |
| 2004/0195055 A1* | 10/2004 | Gilles | F16D 65/18 188/73.1 |
| 2005/0006296 A1 | 1/2005 | Sullivan | |
| 2005/0010190 A1 | 1/2005 | Yeakley | |
| 2005/0045548 A1 | 3/2005 | Brugger | |
| 2005/0070837 A1 | 3/2005 | Ferrarini | |
| 2005/0086008 A1 | 4/2005 | DiGianfilippo | |
| 2005/0092079 A1* | 5/2005 | Ales | F16K 7/14 73/270 |
| 2005/0101901 A1 | 5/2005 | Gura | |
| 2005/0113734 A1 | 5/2005 | Brugger | |
| 2005/0131332 A1 | 6/2005 | Kelly | |
| 2005/0133439 A1 | 6/2005 | Blickhan | |
| 2005/0150309 A1 | 7/2005 | Beard | |
| 2005/0209547 A1 | 9/2005 | Burbank | |
| 2005/0230292 A1 | 10/2005 | Beden | |
| 2005/0240233 A1 | 10/2005 | Lippert | |
| 2006/0064053 A1 | 3/2006 | Bollish | |
| 2006/0091056 A1 | 5/2006 | Brugger | |
| 2006/0113249 A1 | 6/2006 | Childers | |
| 2006/0117859 A1 | 6/2006 | Liu | |
| 2006/0122552 A1* | 6/2006 | O'Mahony | A61M 1/34 604/6.11 |
| 2006/0195064 A1 | 8/2006 | Plahey | |
| 2006/0226057 A1 | 10/2006 | Robinson | |
| 2006/0226090 A1 | 10/2006 | Robinson | |
| 2006/0241543 A1 | 10/2006 | Gura | |
| 2006/0289342 A1 | 12/2006 | Sugioka | |
| 2007/0060786 A1 | 3/2007 | Gura | |
| 2007/0088333 A1 | 4/2007 | Levin | |
| 2007/0112297 A1 | 5/2007 | Plahey | |
| 2007/0158249 A1 | 7/2007 | Ash | |
| 2007/0158268 A1 | 7/2007 | DeComo | |
| 2007/0161113 A1 | 7/2007 | Ash | |
| 2007/0179425 A1 | 8/2007 | Gura | |
| 2007/0213654 A1 | 9/2007 | Lundtveit | |
| 2007/0253463 A1 | 11/2007 | Perry | |
| 2007/0276328 A1 | 11/2007 | Childers | |
| 2008/0006570 A1 | 1/2008 | Gura | |
| 2008/0021366 A1 | 1/2008 | Gura | |
| 2008/0041136 A1 | 2/2008 | Kopelman | |
| 2008/0041792 A1 | 2/2008 | Crnkovich | |
| 2008/0051689 A1 | 2/2008 | Gura | |
| 2008/0058696 A1 | 3/2008 | Gura | |
| 2008/0065006 A1 | 3/2008 | Roger | |
| 2008/0077068 A1 | 3/2008 | Orr | |
| 2008/0149563 A1 | 6/2008 | Ash | |
| 2008/0195021 A1 | 8/2008 | Roger | |
| 2008/0195060 A1 | 8/2008 | Roger | |
| 2008/0208103 A1 | 8/2008 | Demers | |
| 2008/0217245 A1 | 9/2008 | Rambod | |
| 2008/0230450 A1 | 9/2008 | Burbank | |
| 2008/0258735 A1 | 10/2008 | Quackenbush | |
| 2008/0264498 A1 | 10/2008 | Thompson | |
| 2008/0290974 A1 | 11/2008 | Adams | |
| 2009/0004053 A1 | 1/2009 | Kenley | |
| 2009/0008306 A1 | 1/2009 | Cicchello | |
| 2009/0008331 A1 | 1/2009 | Wilt | |
| 2009/0010627 A1 | 1/2009 | Lindsay | |
| 2009/0076434 A1 | 3/2009 | Mischelevich | |
| 2009/0079578 A1 | 3/2009 | Dvorsky | |
| 2009/0080757 A1 | 3/2009 | Roger | |
| 2009/0082646 A1 | 3/2009 | Bouton | |
| 2009/0082647 A1 | 3/2009 | Busby | |
| 2009/0082649 A1 | 3/2009 | Muller | |
| 2009/0082653 A1 | 3/2009 | Rohde | |
| 2009/0082676 A1 | 3/2009 | Bennison | |
| 2009/0083331 A1 | 3/2009 | Oh | |
| 2009/0095679 A1 | 4/2009 | Demers | |
| 2009/0101549 A1 | 4/2009 | Kamen | |
| 2009/0101552 A1 | 4/2009 | Fulkerson | |
| 2009/0101577 A1 | 4/2009 | Fulkerson | |
| 2009/0105627 A1 | 4/2009 | Rohde | |
| 2009/0107902 A1 | 4/2009 | Childers | |
| 2009/0112155 A1* | 4/2009 | Zhao | A61M 5/14212 604/67 |
| 2009/0112507 A1 | 4/2009 | Edney | |
| 2009/0113335 A1 | 4/2009 | Sandoe | |
| 2009/0114037 A1 | 5/2009 | Smith | |
| 2009/0120864 A1 | 5/2009 | Fulkerson | |
| 2009/0124963 A1* | 5/2009 | Hogard | A61M 1/16 604/30 |
| 2009/0127193 A1 | 5/2009 | Updyke | |
| 2009/0127793 A1 | 5/2009 | Ferris | |
| 2009/0137940 A1 | 5/2009 | Orr | |
| 2009/0173682 A1 | 7/2009 | Robinson | |
| 2009/0282980 A1 | 11/2009 | Gura | |
| 2009/0312694 A1 | 12/2009 | Bedingfield | |
| 2010/0022936 A1 | 1/2010 | Gura | |
| 2010/0078381 A1 | 4/2010 | Merchant | |
| 2010/0078387 A1 | 4/2010 | Wong | |
| 2010/0084330 A1 | 4/2010 | Wong | |
| 2010/0094193 A1 | 4/2010 | Gura | |

(56) References Cited

U.S. PATENT DOCUMENTS

| | | |
|---|---|---|
| 2010/0100034 A1 | 4/2010 | Wich-Heiter |
| 2010/0101664 A1* | 4/2010 | Yamamoto ............. F16K 7/045 137/486 |
| 2010/0116048 A1 | 5/2010 | Fulkerson |
| 2010/0116740 A1 | 5/2010 | Fulkerson |
| 2010/0129247 A1 | 5/2010 | Lauer |
| 2010/0133153 A1 | 6/2010 | Beden |
| 2010/0140149 A1 | 6/2010 | Fulkerson |
| 2010/0179464 A1 | 7/2010 | Smith |
| 2010/0184198 A1 | 7/2010 | Joseph |
| 2010/0192686 A1 | 8/2010 | Kamen |
| 2010/0209300 A1 | 8/2010 | Dirac |
| 2010/0234786 A1 | 9/2010 | Fulkerson |
| 2010/0252490 A1 | 10/2010 | Fulkerson |
| 2010/0312161 A1 | 12/2010 | Jonsson |
| 2010/0326911 A1 | 12/2010 | Rosenbaum |
| 2010/0326916 A1 | 12/2010 | Wrazel |
| 2010/0331754 A1 | 12/2010 | Fulkerson |
| 2011/0000830 A1 | 1/2011 | Ikeda |
| 2011/0000832 A1 | 1/2011 | Kelly |
| 2011/0009799 A1 | 1/2011 | Mullick |
| 2011/0017665 A1 | 1/2011 | Updyke |
| 2011/0028881 A1 | 2/2011 | Basaglia |
| 2011/0028882 A1 | 2/2011 | Basaglia |
| 2011/0041928 A1 | 2/2011 | Volker |
| 2011/0046533 A1 | 2/2011 | Stefani |
| 2011/0054352 A1 | 3/2011 | Ko |
| 2011/0054378 A1 | 3/2011 | Fulkerson |
| 2011/0071465 A1 | 3/2011 | Wang |
| 2011/0083746 A1* | 4/2011 | Hoang .................. F16K 3/0254 137/1 |
| 2011/0087187 A1 | 4/2011 | Beck |
| 2011/0092907 A1 | 4/2011 | Krogh |
| 2011/0093294 A1 | 4/2011 | Elahi |
| 2011/0098545 A1 | 4/2011 | Ross |
| 2011/0098624 A1 | 4/2011 | McCotter |
| 2011/0098625 A1 | 4/2011 | Masala |
| 2011/0098635 A1 | 4/2011 | Helmore |
| 2011/0105877 A1 | 5/2011 | Wilt |
| 2011/0105981 A1 | 5/2011 | Wagner |
| 2011/0105983 A1 | 5/2011 | Kelly |
| 2011/0105984 A1 | 5/2011 | Patel |
| 2011/0106002 A1 | 5/2011 | Helmore |
| 2011/0106047 A1 | 5/2011 | Burbank |
| 2011/0106466 A1 | 5/2011 | Furmanksi |
| 2011/0107251 A1 | 5/2011 | Guaitoli |
| 2011/0108482 A1 | 5/2011 | Lovell |
| 2011/0125073 A1 | 5/2011 | Rambod |
| 2011/0126714 A1 | 6/2011 | Brugger |
| 2011/0132838 A1 | 6/2011 | Curtis |
| 2011/0132841 A1 | 6/2011 | Rohde |
| 2011/0137224 A1 | 6/2011 | Ibragimov |
| 2011/0137264 A1 | 6/2011 | Chelak |
| 2011/0139704 A1 | 6/2011 | Choi |
| 2011/0140896 A1 | 6/2011 | Menzel |
| 2011/0141116 A1 | 6/2011 | Dalesch |
| 2011/0152739 A1 | 6/2011 | Roncadi |
| 2011/0155657 A1 | 6/2011 | Collins |
| 2011/0160649 A1 | 6/2011 | Pan |
| 2011/0166507 A1 | 7/2011 | Childers |
| 2011/0168614 A1 | 7/2011 | Pouchoulin |
| 2011/0171713 A1 | 7/2011 | Bluchel |
| 2011/0189048 A1 | 8/2011 | Curtis |
| 2011/0208072 A1 | 8/2011 | Pfeiffer |
| 2011/0208106 A1 | 8/2011 | Levin |
| 2011/0213289 A1 | 9/2011 | Toyoda |
| 2011/0218475 A1 | 9/2011 | Brugger |
| 2011/0218487 A1 | 9/2011 | Shang |
| 2011/0226680 A1 | 9/2011 | Jonsson |
| 2011/0230814 A1 | 9/2011 | Kopperschmidt |
| 2011/0232388 A1 | 9/2011 | Butterfield |
| 2011/0237997 A1 | 9/2011 | Beden |
| 2011/0237998 A1 | 9/2011 | Wariar |
| 2011/0240537 A1 | 10/2011 | Ferrarini |
| 2011/0240555 A1 | 10/2011 | Ficheux |
| 2011/0269167 A1 | 11/2011 | Bene |
| 2011/0272337 A1 | 11/2011 | Palmer |
| 2011/0272352 A1 | 11/2011 | Braig |
| 2011/0275984 A1 | 11/2011 | Biewer |
| 2011/0284464 A1 | 11/2011 | Roncadi |
| 2011/0297593 A1 | 12/2011 | Kelly |
| 2011/0297598 A1 | 12/2011 | Lo |
| 2011/0297599 A1 | 12/2011 | Lo |
| 2011/0300010 A1 | 12/2011 | Jamagin |
| 2011/0300230 A1 | 12/2011 | Peterson |
| 2011/0303588 A1 | 12/2011 | Kelly |
| 2011/0303590 A1 | 12/2011 | Childers |
| 2011/0303598 A1 | 12/2011 | Lo |
| 2011/0309019 A1 | 12/2011 | Ahrens |
| 2011/0315611 A1 | 12/2011 | Fulkerson |
| 2011/0319823 A1* | 12/2011 | Bojan .................. A61M 5/142 604/151 |
| 2012/0010554 A1 | 1/2012 | Vantard |
| 2012/0018377 A1 | 1/2012 | Tsukamoto |
| 2012/0018378 A1 | 1/2012 | Kelly |
| 2012/0022440 A1 | 1/2012 | Childers |
| 2012/0029324 A1 | 2/2012 | Akonur |
| 2012/0029937 A1 | 2/2012 | Neftel |
| 2012/0031826 A1 | 2/2012 | Childers |
| 2012/0035534 A1 | 2/2012 | Yu |
| 2012/0037550 A1 | 2/2012 | Childers |
| 2012/0043279 A1 | 2/2012 | Kelly |
| 2012/0065567 A1 | 3/2012 | Zarate |
| 2012/0075266 A1 | 3/2012 | Shimizu |
| 2012/0214117 A1 | 8/2012 | Broker |
| 2012/0259282 A1* | 10/2012 | Alderete, Jr. ...... A61M 5/14244 604/131 |
| 2013/0126413 A1 | 5/2013 | Van Der Merwe |
| 2013/0140652 A1 | 6/2013 | Erdler |
| 2013/0184638 A1 | 7/2013 | Scarpaci |
| 2013/0199998 A1 | 8/2013 | Kelly |
| 2013/0220907 A1 | 8/2013 | Fulkerson |
| 2013/0233395 A1* | 9/2013 | Dinh ................. H01L 21/02104 137/8 |
| 2013/0292319 A1 | 11/2013 | Fulkerson |
| 2014/0199193 A1 | 7/2014 | Wilt |

FOREIGN PATENT DOCUMENTS

| | | |
|---|---|---|
| CN | 1235849 A | 11/1999 |
| CN | 1471617 A | 1/2004 |
| CN | 101175514 | 5/2008 |
| CN | 101269247 | 9/2008 |
| CN | 101311589 | 11/2008 |
| CN | 101801432 | 8/2010 |
| CN | 201600175 U | 10/2010 |
| CN | 101977642 | 2/2011 |
| CN | 102596283 A | 7/2012 |
| CN | 102639201 A | 8/2012 |
| CN | 103476486 A | 12/2013 |
| EP | 0121085 | 10/1984 |
| EP | 0121085 A1 | 10/1984 |
| EP | 0808633 | 11/1997 |
| EP | 2237814 | 10/2010 |
| GB | 1579177 | 11/1980 |
| JP | S50126866 A | 10/1975 |
| JP | S56138580 U | 10/1981 |
| JP | S5755010 U | 3/1982 |
| JP | S5913770 U | 1/1984 |
| JP | S59127978 U | 8/1984 |
| JP | S6037674 U | 3/1985 |
| JP | S60108870 | 6/1985 |
| JP | S60108870 U | 7/1985 |
| JP | S63202882 A | 8/1988 |
| JP | S63192912 U | 12/1988 |
| JP | H02114269 U | 9/1990 |
| JP | H0413143 U | 2/1992 |
| JP | 005176991 A | 7/1993 |
| JP | H05172268 A | 9/1993 |
| JP | H06230023 A | 8/1994 |
| JP | H07504507 A | 5/1995 |
| JP | H08511094 | 11/1996 |
| JP | H11137673 A | 5/1999 |
| JP | 2002119585 A | 4/2002 |

(56) References Cited

FOREIGN PATENT DOCUMENTS

| | | | |
|---|---|---|---|
| JP | 2002139165 A | * | 5/2002 |
| JP | 2002523772 | | 7/2002 |
| JP | 2003502091 | | 1/2003 |
| JP | 2004057284 | | 2/2004 |
| JP | 3126509 U | | 11/2006 |
| JP | 2008055185 A | | 3/2008 |
| JP | 2008291911 A | | 4/2008 |
| JP | 2008511094 A | | 4/2008 |
| JP | 2008531192 | | 8/2008 |
| JP | 2008531192 A | | 8/2008 |
| JP | 2008531192 A1 | | 8/2008 |
| JP | 2009521965 | | 6/2009 |
| JP | 2012510826 A | | 5/2012 |
| MX | 20103880 | | 7/2010 |
| TW | 200824731 A | | 6/2008 |
| WO | 1980002806 | | 12/1980 |
| WO | 9318380 A1 | | 9/1993 |
| WO | 199318380 | | 9/1993 |
| WO | 1993018380 A1 | | 9/1993 |
| WO | 9420154 A1 | | 9/1994 |
| WO | 9428386 A1 | | 12/1994 |
| WO | 199428386 | | 12/1994 |
| WO | 1996025214 | | 8/1996 |
| WO | 1997027490 | | 7/1997 |
| WO | 9823353 | | 6/1998 |
| WO | 1999030757 A1 | | 6/1999 |
| WO | 0021590 A1 | | 4/2000 |
| WO | 20015069412 A1 | | 7/2001 |
| WO | 2003099354 | | 12/2003 |
| WO | 2003101510 A1 | | 12/2003 |
| WO | 2004009158 A2 | | 1/2004 |
| WO | 2005065126 A2 | | 7/2005 |
| WO | 2005089832 A2 | | 9/2005 |
| WO | 200609362 | | 9/2006 |
| WO | 2006120415 | | 11/2006 |
| WO | 2007028056 | | 3/2007 |
| WO | 2007140241 A1 | | 12/2007 |
| WO | 2008053259 A1 | | 5/2008 |
| WO | 2008129830 A1 | | 10/2008 |
| WO | 2009042181 A1 | | 4/2009 |
| WO | 2009045589 A2 | | 4/2009 |
| WO | 2009065598 | | 5/2009 |
| WO | 2009073567 | | 6/2009 |
| WO | 2009091963 | | 7/2009 |
| WO | 2009157877 | | 12/2009 |
| WO | 201042666 A2 | | 4/2010 |
| WO | 2010042666 | | 4/2010 |
| WO | 2010042667 | | 4/2010 |
| WO | 2010062698 | | 6/2010 |
| WO | 2010062698 A2 | | 6/2010 |
| WO | 2010081121 | | 7/2010 |
| WO | 2010081121 A1 | | 7/2010 |
| WO | 2010114932 | | 10/2010 |
| WO | 2012108910 | | 8/2012 |
| WO | 2014105267 A1 | | 7/2014 |
| WO | 2014105755 | | 7/2014 |

OTHER PUBLICATIONS

International Search Report for PCT/US14/60122, dated Jan. 21, 2015.
Anthony J. Wing et al., 'Dialysate Regeneration', Replacement of Renal Function by Dialysis, Chapter 17, 323-340 (William Drukker et al., eds., Martinus Nijhoff Publishers, 2nd ed., 1983).
Reyes et al., 'Acid-Base Derangements During Sorbent Regenerative Hemodialysis in Mechanically Ventilated Patients', Critical Care Medicine, vol. 19, No. 4, 1991, 554-559 (col. 2, lines 17-22).
Fresenius AG, 'Acumen Acute Dialysis Machine Operating Instructions', Version 1.0, May 1996.
Cobe Laboratories, Inc., 'CentrySystem 3 Dialysis Control Unit Operators Manual', Sep. 1988.
Ward et al., 'Sorbent Dialysis Regenerated Dialysis Delivery Systems', Peritoneal Dialysis Bulletin, Chapter 8, 3(2): S41-S48 (Apr.-Jun. 1983).
Renal Solutions, Inc., 510(K) for the SORB+ and HISORB+ Cartridges, Mar. 31, 2003.
CD Medical, Inc., 'Operator's Manual Drake Willock 480 Ultrafiltration Control Single Patient Delivery System', 1988.
NxStage Medical, Inc., 'NxStage System One User's Guide', Software Version 4.3, Part 1 through Part 6-20, 2006.
NxStage Medical, Inc., 'NxStage System One User's Guide', Software Version 4.3, Part 6-20 through Part C-17, 2006.
Manns et al., 'The acu-men: A New Device for Continuous Renal Replacement Therapy in Acute Renal Failure', Kidney International, vol. 54 (1998), 268-274.
Renal Solutions, Inc., Portions of 510(k) Allient Sorbent Hemodialysis System (Sections A-I), Dec. 17, 2004.
Renal Solutions, Inc., Portions of 510(k) Allient Sorbent Hemodialysis System (Allient Main Controller Software Architecture Overview), Renal Solutions, Inc., Dec. 17, 2004.
Renal Solutions, Inc., Portions of 510(k) Allient Sorbent Hemodialysis System (Sections M.3 and M.4), Renal Solutions, Inc., Dec. 17, 2004.
Renal Solutions, Portions of the Allient Sorbent Hemodialysis System, Home User Manual, 2006, Chapters 1-3.
Renal Solutions, Portions of the Allient Sorbent Hemodialysis System, Home User Manual, 2006, Chapters 4.
Renal Solutions, Portions of the Allient Sorbent Hemodialysis System, Home User Manual, 2006, Chapters 5 to end.
Renal Solutions, Portions of the Allient Sorbent Hemodialysis System, Operator Manual, 2008, Chapters 1 to 2.
Renal Solutions, Portions of the Allient Sorbent Hemodialysis System, Operator Manual, 2008, Chapter 3.
Renal Solutions, Portions of the Allient Sorbent Hemodialysis System, Operator Manual, 2008, Chapter 4, 4-1 to 4-33.
Renal Solutions, Portions of the Allient Sorbent Hemodialysis System, Operator Manual, 2008, Chapter 4, 4-34 to 4-69.
Renal Solutions, Portions of the Allient Sorbent Hemodialysis System, Operator Manual, 2008, Chapter 5.
Renal Solutions, Portions of the Allient Sorbent Hemodialysis System, Operator Manual Model 1500, 2008, Chapters 1 to 2.
Renal Solutions, Portions of the Allient Sorbent Hemodialysis System, Operator Manual Model 1500, 2008, Chapter 3, 3-2 to 3-30.
Renal Solutions, Portions of the Allient Sorbent Hemodialysis System, Operator Manual Model 1500, 2008, Chapter 3, 3-31 to 3-70.
Fresenius USA, Inc., "Fresenius 2008H Hemodialysis Machine", Part No. 490005, Revision H, 1994-2001.
Renal Solutions, Inc., 'Dialysate Tubing Set and Dialysate Reservoir Bag for the Allient Sorbent Hemodialysis System', Instructions, 2004.
REDY 2000 Operators Manual (1991) (Sorbent cartridge-based hemodialysis system).
REDY 2000 Service Manual (1989) (Sorbent cartridge-based hemodialysis system).
Seratron Dialysis Control System Operations Manual (cumulative 1980).
Renal Solutions, Special 510(k) Device Modification, Allient Sorbent Hemodialysis System, Mar. 15, 2007.
COBE Renal Care, Inc., "Sorbent Dialysis Primer", Edition 4, Sep. 1993.

* cited by examiner

VALVE SYSTEM WITH A PRESSURE SENSING DISPLACEMENT MEMBER

CROSS-REFERENCE

The present application is a continuation application of U.S. patent application Ser. No. 15/139,144, entitled "Smart Actuator For Valve" and filed on Apr. 26, 2016, which is a continuation application of U.S. patent application Ser. No. 14/077,112, of the same title, filed on Nov. 11, 2013, and issued as U.S. Pat. No. 9,354,640 on May 31, 2016. The above applications are herein incorporated by reference in their entirety.

FIELD

The present specification relates generally to valves used in fluid circuits. More particularly, the present specification relates to an actuator mechanism for a valve having feedback control provided by a pressure transducer and/or force gauge located on the contact end of the actuator.

BACKGROUND

Valves in fluid circuits typically have an open state and a closed state, which is achieved by causing a linear actuator to extend towards, and press against, a membrane or diaphragm. In response, the diaphragm pushes into an orifice in the fluid pathway. The actuator continues to push the diaphragm into the orifice until the diaphragms contacts a valve seat opposite the actuator, thereby occluding fluid flow and closing the valve. The reverse process, namely moving the actuator away from the diaphragm and thereby releasing the diaphragm from compression against the valve seat, opens the orifice and permits fluid to flow. The linear actuator is typically driven by a stepper motor and/or DC motor operated by a controller. The system is preferably lightweight and consumes minimum power, making it ideal for use in a variety of applications. The system can be used in conjunction with an orifice in any structure. In particular, an orifice is any hole, opening, void, or partition in any type of material. This includes pathways in tubing, manifolds, disposable manifolds, channels, and other pathways.

Blood purification systems, which are used for conducting hemodialysis, hemodiafiltration or hemofiltration, involve the extracorporeal circulation of blood through an exchanger having a semi permeable membrane. Such systems further include a hydraulic system for circulating blood and a hydraulic system for circulating replacement fluid or dialysate comprising the certain blood electrolytes in concentrations close to those of the blood of a healthy subject. Flow in the fluid circuits is controlled by valves positioned in the fluid flow pathway. Examples of such fluid pathways include those disclosed in U.S. patent application Ser. No. 13/023,490, assigned to the applicant of the present invention, entitled "Portable Dialysis Machine" and filed on Feb. 8, 2011, which is incorporated herein by reference.

The valves are preferably implemented in a manifold using elastic membranes at flow control points which are selectively occluded, as required, by protrusions, pins, or other members extending from the manifold machine. In some dialysis machines, fluid occlusion is enabled using a safe, low-energy magnetic valve. Current valve systems often use a sensor, preferably an optical sensor, to determine the state of the valve (open or closed).

While the optical sensor is useful for determining the open or closed state of the valve and the position of the plunger, the prior art lacks a consistent and reliable mechanism for controlling the valve amidst changes in the valve system. Current linear actuators do not include a means for determining where or when to precisely stop pushing against the diaphragm (or membrane) in closing the valve, when to increase pressure to the diaphragm to keep the valve closed, or when to decrease pressure to a diaphragm that is being pulled via vacuum action in the fluid circuit. For example, over time, the diaphragm undergoes structural changes due to exposure to sterilization methods, temperature exposure, repeated strain, and pressure fluctuations within the system. Typically, the diaphragm material softens and thins. As these changes occur, moving the actuator to the same position results in incomplete shut-off of fluid flow. The actuator must be advanced further into the diaphragm to achieve the same level of valve closure.

A liner actuator driven by a stepper motor and/or DC motor operated by a controller can be used to deliver incremental changes to the actuator position. However, neither of these mechanisms allow for feedback control of actuator position through pressure or force sensing. Therefore, what is needed is an actuator mechanism for a manifold membrane/diaphragm type valve that allows for control of the positioning of the actuator based on feedback provided by a sensor located on the contact end of the actuator.

SUMMARY

The present specification discloses a valve actuator system adapted to open and close a valve, comprising an orifice closing member, positioned within a manifold and adjacent a fluid pathway through which fluid flows in a dialysis system, said valve actuator mechanism comprising: a displacement member adapted to being displaced linearly and having a contact end wherein said contact end is positioned proximate to said orifice closing member when said valve is in said open state; a motor for moving said displacement member; at least one pressure sensor positioned on said contact end for sensing pressure generated when said contact end is in physical communication with said orifice closing member and for relaying data based on said sensed pressure; and a controller for receiving the sensed pressure from the at least one pressure sensor, wherein said controller comprises a memory having stored therein a plurality of programmatic instructions that, when executed by a processing unit, compare said sensed pressure to a pre-determined value stored in said memory and activate said motor to move said displacement member toward or away from said orifice closing member to optimally position the contact end against said orifice closing member.

The present specification also discloses a valve actuator system adapted to open and close a valve, comprising an orifice closing member, positioned within a manifold and adjacent a fluid pathway through which fluid flows in a dialysis system, said valve actuator mechanism comprising: a displacement member adapted to being displaced linearly and having a contact end wherein said contact end is positioned proximate to said orifice closing member when said valve is in said open state; a motor for moving said displacement member; at least one force sensor positioned on said contact end for sensing force generated when said contact end is in physical communication with said orifice closing member and for relaying data based on said sensed force; and a controller for receiving the sensed force from the at least one force sensor, wherein said controller comprises a memory having stored therein a plurality of programmatic instructions that, when executed by a processing unit, compare said sensed force to a pre-determined value stored in said memory and activate said motor to move said displacement member toward or away from said orifice closing member to optimally position the contact end against said orifice closing member.

The present specification also discloses a valve actuator system adapted to open and close a valve, comprising an orifice closing member, positioned within a manifold and adjacent a fluid pathway through which fluid flows in a dialysis system, said valve actuator mechanism comprising: a displacement member adapted to being displaced linearly and having a contact end wherein said contact end is positioned proximate to said orifice closing member when said valve is in said open state; a motor for moving said displacement member; at least one pressure sensor positioned on said contact end for sensing pressure generated when said contact end is in physical communication with said orifice closing member and for relaying data based on said sensed pressure; at least one force gauge positioned on said contact end for sensing force generated when said contact end is in physical communication with said orifice closing member and for relaying data based on said sensed force; and a controller for receiving the sensed pressure from the at least one pressure sensor and the sensed force from the at least one force gauge, wherein said controller comprises a memory having stored therein a plurality of programmatic instructions that, when executed by a processing unit, compare said sensed pressure to a pre-determined pressure value stored in said memory and said sensed force to a pre-determined force value stored is said memory and activate said motor to move said displacement member toward or away from said orifice closing member to optimally position the contact end against said orifice closing member.

In various embodiments, the motor of any of the above valve actuator systems comprises a stepper motor. In other various embodiments, the motor of any of the above valve actuator systems comprises a DC motor.

In various embodiments, any of the above valve actuator systems further comprises an encoder for determining the amount of movement of said displacement member.

In various embodiments, any of the above valve actuator systems is used in a dialysis machine. In various embodiments, when used in a dialysis machine, the controller of the valve actuator system is programmed to maintain a sensed pressure of at least 2 psi. In various embodiments, when used in a dialysis machine, the controller of the valve actuator system is programmed to maintain a force of at least 5 pound-force ($lb_F$).

The present specification also discloses a method of controlling a valve state of a fluid circuit, said method comprising the steps of: providing a valve component having an open position and a closed position and comprising a controller and an orifice closing member adjacent to an orifice through which fluid can flow; providing an actuator mechanism comprising: a displacement member having a contact end, wherein said contact end is adjacent to said orifice closing member when said valve component is in said open position; a motor to exert a linear force on said displacement member to move said contact end of said displacement member against said orifice closing member and cause said orifice closing member to close said orifice; and, at least one sensor positioned on said contact end for sensing a parameter applied to said contact end of said displacement member by said orifice closing member; activating said controller to instruct said actuator mechanism to move said displacement member toward and against said orifice closing member such that said displacement member pushes said orifice closing member into said orifice; sensing at least one parameter applied by said orifice closing member against said contact end of said displacement member using said sensor; relaying data regarding said sensed parameter from said sensor to said controller; comparing said data to pre-determined values stored on said controller, wherein said controller comprises a processing unit and a memory having stored therein a plurality of programmatic instructions and said pre-determined values; and, executing said programmatic instructions based on said comparison to activate said actuator mechanism to move said displacement member further toward or away from said orifice closing member such that said orifice is substantially closed, thereby maintaining a closing force.

In one embodiment, said at least one sensor comprises a pressure transducer and said at least one parameter comprises pressure. In another embodiment, said at least one sensor comprises a force gauge and said at least one parameter comprises force. In yet another embodiment, said at least one sensor comprises a pressure transducer and a force gauge and said at least one parameter comprises pressure and force.

In one embodiment, the method further comprises the step of sensing said at least one parameter while said contact end of said displacement member is adjacent to said orifice closing member when said valve is in said open position and prior to activating said controller to instruct said actuator mechanism to move said displacement member toward and against said orifice closing member.

The aforementioned and other embodiments of the present invention shall be described in greater depth in the drawings and detailed description provided below.

BRIEF DESCRIPTION OF THE DRAWINGS

These and other features and advantages of the present invention will be further appreciated, as they become better understood by reference to the detailed description when considered in connection with the accompanying drawings.

DETAILED DESCRIPTION

Figure 1A:
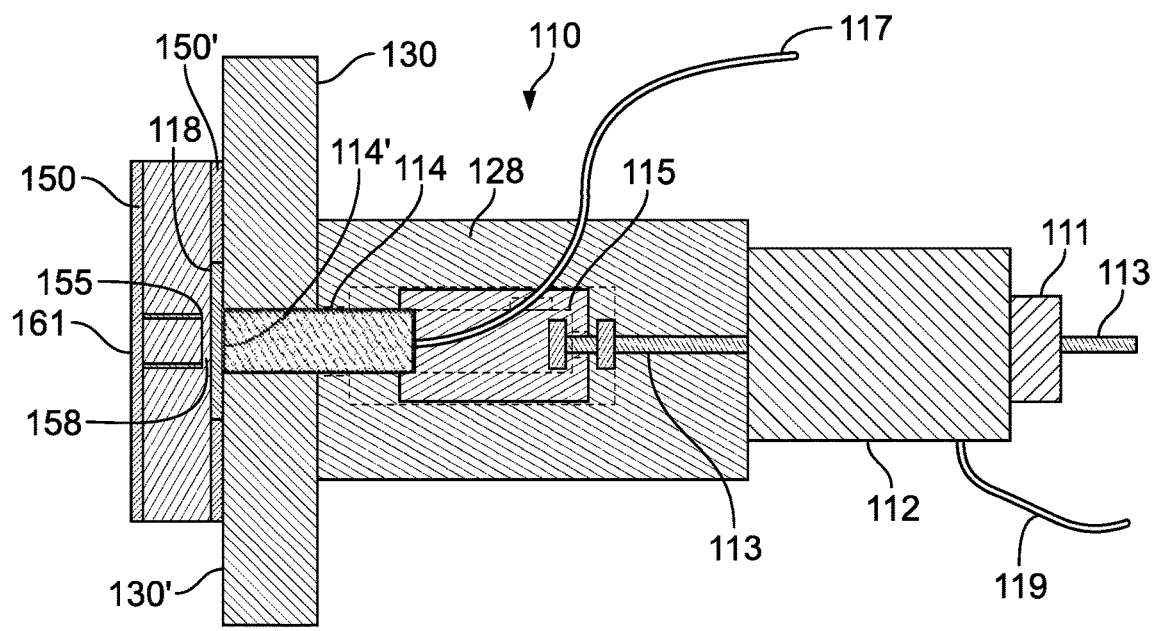
FIG. 1A is an illustration of an actuator mechanism with feedback control, comprising a pressure transducer, and an open valve of a fluid circuit, in accordance with one embodiment of the present specification.

The present specification discloses a system and a method of controlling actuator position for a diaphragm type valve of a fluid circuit based on feedback provided by a pressure transducer and/or force gauge located on the contact end of the actuator. In various embodiments, as a control signal and/or a voltage signal is applied to the linear actuator to cause the actuator to move to close the valve, a pressure transducer or force gauge senses the feedback pressure or opposing applied force from the surface of the diaphragm. The sensed pressure or force is relayed via firmware to a controller which then instructs the actuator to move forward or backward an appropriate distance to maintain a constant pressure or force. As such, temperature and pressure changes in the system and material changes to the diaphragm are sensed immediately and positioning correction is applied to the actuator in real-time, thereby maintaining the same valve state. In addition, changes due to the diaphragm as a result of exposure to sterilization methods can be accounted for during operation. The linear actuator functions as a 'smart' actuator, capable of fine tune adjustments without additional outside monitoring and provides a more accurate and reliable method of closing the valve. In various embodiments, the actuator accommodates changes in force, pressure, temperature, flow, and/or viscosity of the fluid by continuously monitoring pressure and/or force at its contact end.

The actuator is programmed to advance and engage the membrane or diaphragm of a valve of a fluid circuit. As the actuator is advanced, it pushes the diaphragm into the valve orifice until the diaphragm comes into physical contact with a valve seat, thereby sealing the orifice and closing the valve. The actuator includes a contact end that comes into physical contact with the diaphragm and, in one embodiment, comprises a pressure transducer on the contact end.

Upon initial engagement of the diaphragm via the pressure transducer, a voltage signal input (feedback) to the controller is produced. This feedback, a positive voltage type or voltage increase, communicates to the controller that the actuator has located the diaphragm. The controller then controls the actuator, via firmware, to reverse direction until the point of 0 volts (no contact) feedback to the controller. This puts the pressure sensor in an optimum sensing position because the actuator was extended until contact (positive voltage) was achieved and then incrementally retracted such that no positive voltage offset is being sent to the controller. Accordingly, the controller firmware does not have to negate this offset voltage.

When the controller is engaging the actuator to close the valve port that the diaphragm is covering, the actuator linearly pushes up against the diaphragm until the diaphragm engages the port/valve orifice, thus closing off any fluid flow. During the engagement of closing the valve, the positive voltage increases from the pressure transducer to a known closure value (an experimentally derived predetermined value) to close off the valve. If, during the course of operation, the diaphragm begins to thin or soften due to temperature changes or other effects, the pressure transducer will sense a decrease in pressure at the contact end of the actuator. This decrease in pressure will translate to a decrease in positive voltage which will be relayed to the controller. The controller will then instruct the actuator to extend further until the voltage value once again matches the known closure value, signifying that the weakened diaphragm has been pushed further onto the valve seat to ensure complete valve closure. When the controller engages the actuator to open the valve port that the diaphragm is covering, the actuator moves linearly in the opposite direction (backwards away from the diaphragm) until the diaphragm releases from the port/valve orifice, thus allowing the flow of fluid through the space between the diaphragm and the valve port. As the diaphragm moves away from the valve port, the sensed pressure will decrease, signifying that the valve has been returned to an open state.

In various embodiments, the controller can be executed entirely in hardware or in software stored in a memory that may be local to, or remote from, the valve actuator mechanism. The controller steps are achieved by a processor executing the software stored in said memory wherein said memory includes a plurality of programmatic instructions. The processor receives data from the pressure transducer and, based upon a comparison of said data to pre-determined pressure values, executes the software stored in the memory to maintain the valve in a closed state. The processor is also capable of receiving commands from a user via a user interface to open or close the valve. In one embodiment, the controller is a software-based controller that is executed by a general processor located entirely within a controller unit of a dialysis machine.

In another embodiment, the actuator comprises a force gauge on the contact face. Upon initial engagement of the diaphragm via the force gauge, a voltage signal input (feedback) to the controller is produced. This feedback, a positive voltage type or voltage increase, tells the controller that the actuator has located the diaphragm. The controller then controls the actuator, via firmware, to reverse direction until the point of 0 volts (no contact) feedback to the controller. This puts the force gauge in an optimum sensing position without having a positive voltage offset being sent to the controller. The controller firmware does not have to negate this offset voltage.

When the controller is engaging the actuator to close the valve port that the diaphragm is covering, the actuator linearly pushes up against the diaphragm until the diaphragm engages the port/valve orifice, thus closing off any fluid flow. During the engagement of closing the valve, the positive voltage increases from the force gauge to a known closure value (an experimentally derived predetermined value) to close off the valve. If, during the course of operation, the diaphragm begins to thin or soften due to temperature changes or other effects, the force gauge will sense a decrease in force at the contact end of the actuator. This decrease in force will translate to a decrease in positive voltage which will be relayed to the controller. The controller will then instruct the actuator to extend further until the voltage value once again matches the known closure value, signifying that the weakened diaphragm has been pushed further onto the valve seat to ensure complete valve closure. When the controller engages the actuator to open the valve port that the diaphragm is covering, the actuator moves linearly in the opposite direction (backwards away from the diaphragm) until the diaphragm releases from the port/valve orifice, thus allowing the flow of fluid through the space between the diaphragm and the valve port. As the diaphragm moves away from the valve port, the sensed force will decrease, signifying that the valve has been returned to an open state.

In various embodiments, the controller can be executed entirely in hardware or in software stored in a memory that may be local to, or remote from, the valve actuator mechanism. The controller steps are achieved by a processor executing the software stored in said memory wherein said memory includes a plurality of programmatic instructions. The processor receives data from the force gauge and, based upon a comparison of said data to pre-determined force values, executes the software stored in the memory to maintain the valve in a closed state. The processor is also capable of receiving commands from a user via a user interface to open or close the valve. In one embodiment, the controller is a software-based controller that is executed by a general processor located entirely within a controller unit of a dialysis machine.

In yet another embodiment, the actuator comprises both a pressure transducer and a force gauge on the contact face. Upon initial engagement of the diaphragm via the pressure transducer and force gauge, the pressure transducer and the force gauge both send a voltage signal input (feedback) to the controller. This feedback, a positive voltage type or voltage increase, tells the controller that the actuator has located the diaphragm. At this point, the controller then controls the actuator, via firmware, to reverse direction until the point of 0 volts (no contact) feedback to the controller. The controller firmware does not have to negate this offset voltage. This puts the pressure sensor and force gauge in an optimum sensing position without having a positive voltage offset being sent to the controller.

When the controller is engaging the actuator to close the valve port that the diaphragm is covering, the actuator linearly pushes up against the diaphragm until the diaphragm engages the port/valve orifice, thus closing off any fluid flow. During the engagement of closing the valve, the positive voltage increases from the pressure transducer and the force gauge to a known closure value (an experimentally derived predetermined value) to close off the valve. If, during the course of operation, the diaphragm begins to thin or soften due to temperature changes or other effects, the pressure transducer will sense a decrease in pressure and the force gauge will sense a decrease in force at the contact end of the actuator. This decrease in pressure and force will translate to decreases in positive voltage which will be relayed to the controller. The controller will then instruct the actuator to extend further until the voltage values once again match the known closure values, signifying that the weakened diaphragm has been pushed further onto the valve seat to ensure complete valve closure. When the controller engages the actuator to open the valve port that the diaphragm is covering, the actuator moves linearly in the opposite direction (backwards away from the diaphragm) until the diaphragm releases from the port/valve orifice, thus allowing the flow of fluid through the space between the diaphragm and the valve port. As the diaphragm moves away from the valve port, the sensed pressure and force will decrease, signifying that the valve has been returned to an open state.

In various embodiments, the controller can be executed entirely in hardware or in software stored in a memory that may be local to, or remote from, the valve actuator mechanism. The controller steps are achieved by a processor executing the software stored in said memory wherein said memory includes a plurality of programmatic instructions. The processor receives data from the pressure transducer and force gauge and, based upon a comparison of said data to pre-determined pressure and force values, executes the software stored in the memory to maintain the valve in a closed state. The processor is also capable of receiving commands from a user via a user interface to open or close the valve. In one embodiment, the controller is a software-based controller that is executed by a general processor located entirely within a controller unit of a dialysis machine.

Upon full closure of the valve, the pressure transducer can monitor fluid pressure that is engaging the face of the pressure transducer while the force gauge monitors the force needed to keep the valve closed due to possible changes in temperature, fluid density changes, and/or media density changes, thus maintaining a constant pressure as sensed by the force gauge. In this position or operational mode, the pressure transducer can monitor the negative or positive pressure of the orifice independently.

In various embodiments, the pressure and/or force sensing can be continuous or performed at specific time intervals and/or incremental stages. For example, pressure and/or force can be sensed every 1 milliseconds, 1 second, 30 seconds, 1 minute, 5 minutes, 30 minutes, 1 hour, or any other time interval. In addition, in various embodiments, pressure and/or force can be sensing can be performed at specific time intervals until the sensed pressure and/or force value crosses a pre-determined threshold after which said sensing switches to continuous. For example, when diaphragm weakening is suspected based on interval pressure or force sensing, the system can switch to continuous sensing to monitor a possibly failing diaphragm to ensure proper valve functioning.

In various embodiments, optimum pressure and/or force levels to ensure proper valve function can be determined based upon a normalization of a final pressure and/or force state relative to any of the earlier sensed pressure and/or force values.

The present specification discloses multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

In various embodiments, the actuator mechanism with feedback control system of the present specification comprises a linear actuator driven by a stepper motor and/or DC motor operated by a controller, wherein the feedback is provided by a pressure transducer and/or force gauge located on the contact end of the actuator. The system is lightweight and consumes minimum power, making it ideal for use in a variety of applications. The system can be used in conjunction with an orifice in any structure. In particular, an orifice is any hole, opening, void, or partition in any type of material. This includes pathways in tubing, manifolds, disposable manifolds, channels, and other pathways.

Figure 1B:
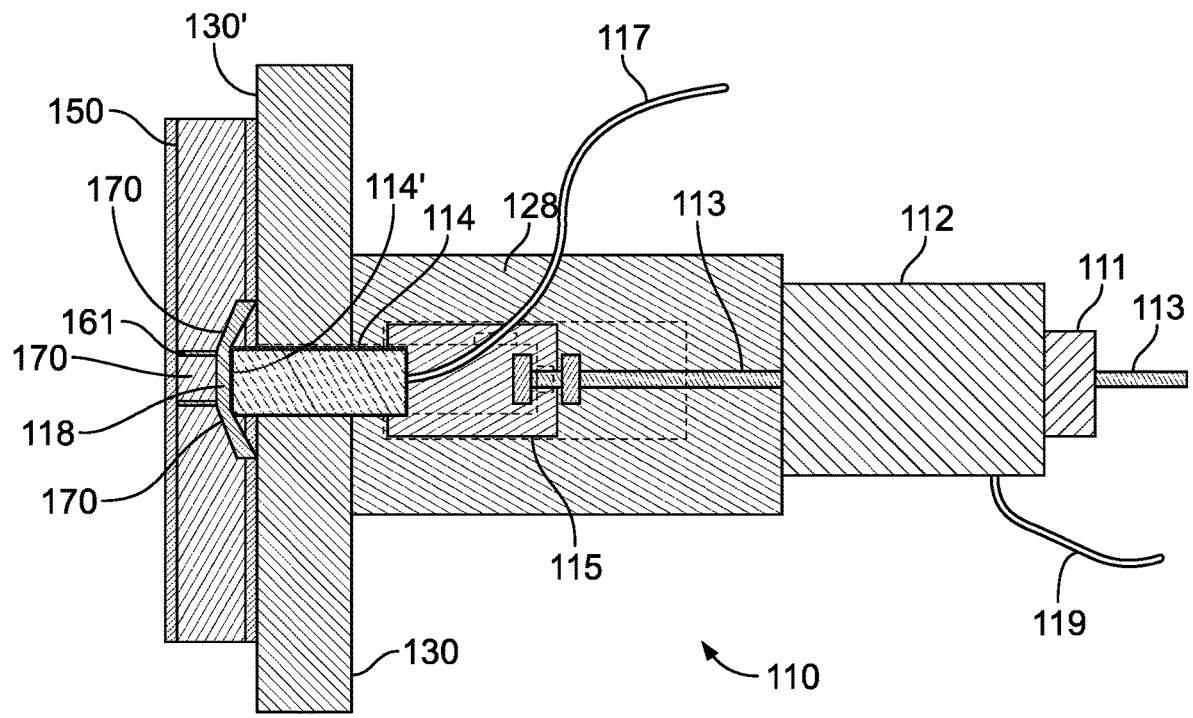
FIG. 1B is an illustration of an actuator mechanism with feedback control, comprising a pressure transducer, and a closed valve of a fluid circuit, in accordance with one embodiment of the present specification.

FIGS. 1A and 1B are illustrations of an actuator mechanism 110 with feedback control, comprising a pressure transducer 114, and an open valve and a closed valve, respectively, of a fluid circuit, in accordance with one embodiment of the present specification. Referring to both FIGS. 1A and 1B simultaneously, each actuator mechanism 110 includes an encoder 111, a stepper or DC linear actuator motor 112, an actuator plunger 113, an actuator mechanism body 128, a pressure transducer 114, and a pressure transducer holder 115. A signal wire 117 connects the pressure transducer 114 to a controller (not shown). A power and signal wire 119 connects the motor 112 to the controller. The encoder 111 acts to notify the system that the actuator mechanism is moving.

Referring to FIG. 1A, the actuator (pressure transducer 114 in this embodiment) is in its 'home' position within the front plate 130 of a machine system. The pressure transducer 114 functions as a linear member contained within a conduit (in this embodiment, a front plate 130 of a machine system) through which it extends axially. Specifically, when the actuator is in its 'home' position, the pressure transducer 114 of the actuator mechanism 110 rests embedded within the front plate 130 of a machine system, such as, in one embodiment, a portion of a dialysis system housing. In one embodiment, when the actuator is in the 'home' position, the pressure transducer 114 rests within the front plate 130 such that the contact end 114' of the pressure transducer 114 is positioned just proximal to, with respect to the actuator mechanism 110, an outer surface 130' of the front plate 130. In other words, when the actuator is in the 'home' position, the contact end 114' of the pressure transducer 114 is slightly recessed within the front plate 130. The pressure transducer 114 is linearly movable within the front plate 130 by activation of the motor 112 and linear movement of the actuator plunger 113 and pressure transducer holder 115. The pressure transducer 114 can be moved forward, with respect to the actuator mechanism 110, such that its contact end 114' extends beyond the outer surface 130' of the front plate 130. A fluid pathway 150 is positioned proximate, or adjacent to, the front plate 130. A diaphragm 118 is positioned in an outer wall 150' of the fluid pathway 150. In one embodiment, the outer wall 150' of the fluid pathway 150 is positioned proximate and adjacent to the outer surface 130' of the front plate 130 such that the diaphragm 118 is proximate to, and in linear alignment with, the pressure transducer 114 of the actuator mechanism 110. Since the actuator mechanism 110 is in the 'home' state, the diaphragm 118 is flat and is not in contact with the pressure transducer 114, and the valve is in the open state. Within the fluid pathway 150, a gap 158 at the valve 161 is present between the diaphragm 118 and valve seat 155, allowing fluid to flow through.

In one embodiment, referring to FIG. 1A, the components of the actuator mechanism 110 are arranged in the following configuration. As mentioned above, in one embodiment, the pressure transducer 114 functions as the actuator. The pressure transducer 114, pressure transducer holder 115, and actuator plunger 113 are linearly movable as a unit via operation of the motor 112 and extend axially throughout the actuator mechanism 110. Using the diaphragm 118 of the outer wall 150' of the fluid pathway 150 as a reference point, the encoder 111 comprises the distal endpoint of the actuator mechanism 110. In one embodiment, a portion of the actuator plunger 113 extends distally from the distal end of the encoder 111. During operation, as the motor 112 moves the actuator plunger 113 toward the diaphragm 118, the portion of the plunger 113 extending from the distal end of the encoder 111 moves proximally through said encoder 111.

Next to the encoder 111 and at a position more proximal to the diaphragm 118 is the motor 112. The plunger 113 extends axially through the motor 112. Positioned proximal to the motor 112 is the actuator mechanism body 128. The distal end of the actuator mechanism body 128 is positioned adjacent to motor 112 and the proximal end of the actuator mechanism 128 is positioned adjacent to the front plate 130 of the machine system. A proximal portion of the actuator plunger 113 extends through the distal portion of the actuator mechanism body 128. Attached to the proximal end of the actuator plunger 113 and housed within the actuator mechanism body 128 is the pressure transducer holder 115. Through action of the motor 112 and extension/retraction of the actuator plunger 113, the pressure transducer holder 115 is linearly movable within the actuator mechanism body 128. Attached to a proximal end of the pressure transducer holder 115 is the pressure transducer 114. The pressure transducer 114 extends axially partially through the actuator mechanism body 128 and partially through the front plate 130. The pressure transducer 114 is linearly movable within the proximal portion of the actuator mechanism body 128 and the front plate 130 via operation of the motor 112 and movement of the actuator plunger 113 and pressure transducer holder 115.

Referring to FIG. 1B, the actuator mechanism 110 is in an 'extended' position with the pressure transducer 114 moved forward through the front plate 130 of the machine system such that the contact end 114' of the pressure transducer 114 extends distally, with respect to the actuator mechanism 110, beyond the outer surface 130' of the front plate 130. The diaphragm 118 has been pushed into the fluid pathway 150 through physical contact with the contact end 114' of the pressure transducer 114. In accordance with various embodiments of the present specification, based on feedback provided to the controller by the pressure transducer 114, the controller has instructed the motor 112 to move the actuator plunger 113 to extend the pressure transducer holder 115 and pressure transducer 114 such that the contact end 114' of the pressure transducer 114 has come into contact with, and pushed forward, the diaphragm 118. The diaphragm 118 is extended into the fluid pathway 150 and is in contact with the valve seat 155, effectively closing the valve 161 and shutting off fluid flow. The gap at valve seat 155, as seen as gap 158 in FIG. 1A, has been closed in FIG. 1B. Pressure 170 increases around the diaphragm 118 and valve seat 155 and pushes against the diaphragm 118.

Figure 2A:
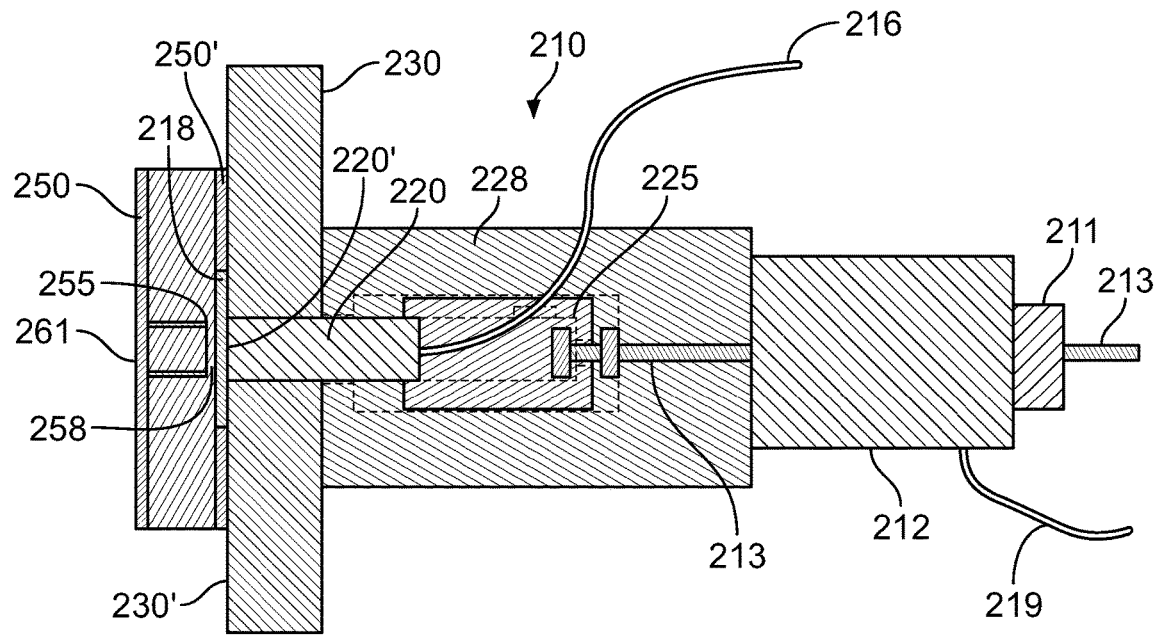
FIG. 2A is an illustration of an actuator mechanism with feedback control, comprising a force gauge, and an open valve of a fluid circuit, in accordance with one embodiment of the present specification.
Figure 2B:
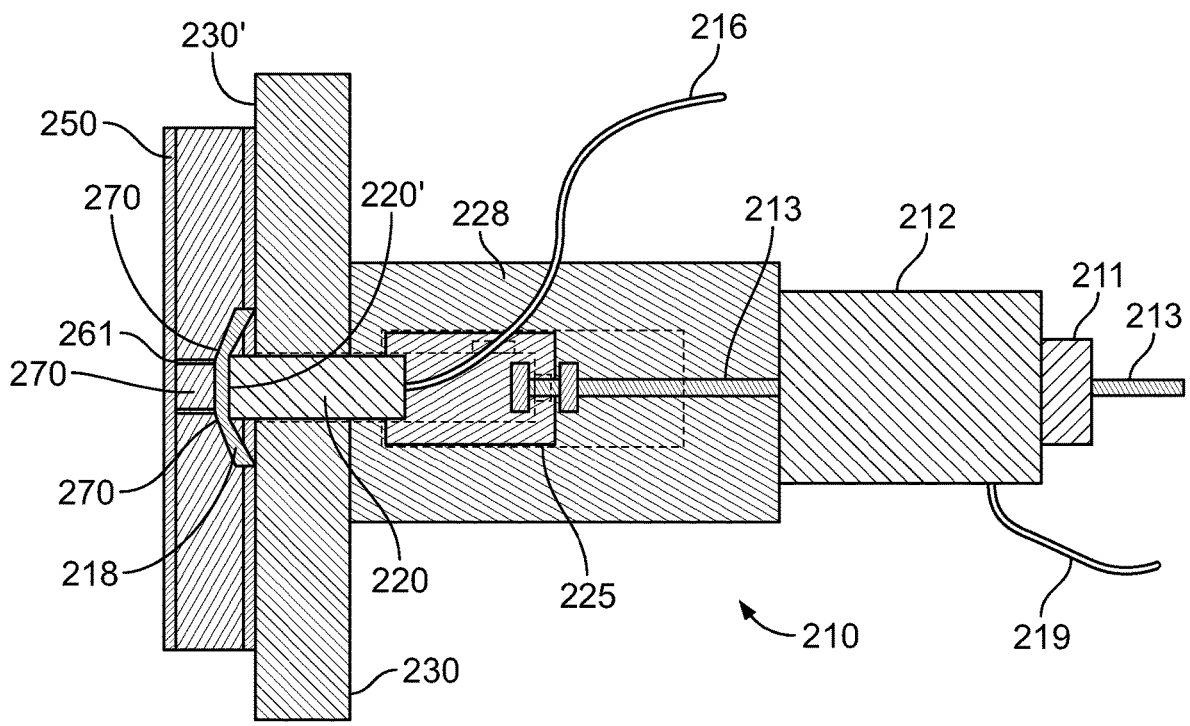
FIG. 2B is an illustration of an actuator mechanism with feedback control, comprising a force gauge, and a closed valve of a fluid circuit, in accordance with one embodiment of the present specification.

FIGS. 2A and 2B are illustrations of an actuator mechanism 210 with feedback control, comprising a force gauge 220, and an open valve and a closed valve, respectively, of a fluid circuit, in accordance with one embodiment of the present specification. Referring to both FIGS. 2A and 2B simultaneously, each actuator mechanism 210 includes an encoder 211, a stepper or DC linear actuator motor 212, an actuator plunger 213, an actuator mechanism body 228, a force gauge 220, and a force gauge holder 225. A signal wire 216 connects the force gauge 220 to a controller (not shown). A power and signal wire 219 connects the motor 212 to the controller. The encoder 211 acts to notify the system that the actuator mechanism is moving.

Referring to FIG. 2A, the actuator (force gauge 220 in this embodiment) is in its 'home' position within the front plate 230 of a machine system. The force gauge 220 functions as a linear member contained within a conduit (in this embodiment, a front plate 230 of a machine system) through which it extends axially. Specifically, when the actuator is in its 'home' position, the force gauge 220 of the actuator mechanism 210 rests embedded within the front plate 230 of a machine system, such as, in one embodiment, a portion of a dialysis system housing. In one embodiment, when the actuator is in the 'home' position, the force gauge 220 rests within the front plate 230 such that the contact end 220' of the force gauge 220 is positioned just proximal to, with respect to the actuator mechanism 210, an outer surface 230' of the front plate 230. In other words, when the actuator is in the 'home' position, the contact end 220' of the force gauge 220 is slightly recessed within the front plate 230. The force gauge 220 is linearly movable within the front plate 230 by activation of the motor 212 and linear movement of the actuator plunger 213 and force gauge holder 225. The force gauge 220 can be moved forward, with respect to the actuator mechanism 210, such that its contact end 220' extends beyond the outer surface 230' of the front plate 230. A fluid pathway 250 is positioned proximate, or adjacent to, the front plate 230. A diaphragm 218 is positioned in an outer wall 250' of the fluid pathway 250. In one embodiment, the outer wall 250' of the fluid pathway 250 is positioned proximate and adjacent to the outer surface 230' of the front plate 230 such that the diaphragm 218 is proximate to, and in linear alignment with, the force gauge 220 of the actuator mechanism 210. Since the actuator mechanism 210 is in the 'home' state, the diaphragm 218 is flat and is not in contact with the force gauge 220, and the valve is in the open state. Within the fluid pathway 250, a gap 258 at the valve 261 is present between the diaphragm 218 and valve seat 255, allowing fluid to flow through.

In one embodiment, referring to FIG. 2A, the components of the actuator mechanism 210 are arranged in the following configuration. As mentioned above, in one embodiment, the force gauge 220 functions as the actuator. The force gauge 220, force gauge holder 225, and actuator plunger 213 are linearly movable as a unit via operation of the motor 212 and extend axially throughout the actuator mechanism 210. Using the diaphragm 218 of the outer wall 250' of the fluid pathway 250 as a reference point, the encoder 211 comprises the distal endpoint of the actuator mechanism 210. In one embodiment, a portion of the actuator plunger 213 extends distally from the distal end of the encoder 211. During operation, as the motor 212 moves the actuator plunger 213 toward the diaphragm 218, the portion of the plunger 213 extending from the distal end of the encoder 211 moves proximally through said encoder 211. Next to the encoder 211 and at a position more proximal to the diaphragm 218 is the motor 212. The plunger 213 extends axially through the motor 212. Positioned proximal to the motor 212 is the actuator mechanism body 228. The distal end of the actuator mechanism body 228 is positioned adjacent to motor 212 and the proximal end of the actuator mechanism 228 is positioned adjacent to the front plate 230 of the machine system. A proximal portion of the actuator plunger 213 extends through the distal portion of the actuator mechanism body 228. Attached to the proximal end of the actuator plunger 213 and housed within the actuator mechanism body 228 is the force gauge holder 225. Through action of the motor 212 and extension/retraction of the actuator plunger 213, the force gauge holder 225 is linearly movable within the actuator mechanism body 228. Attached to a proximal end of the force gauge holder 225 is the force gauge 220. The force gauge 220 extends axially partially through the actuator mechanism body 228 and partially through the front plate 230. The force gauge 220 is linearly movable within the proximal portion of the actuator mechanism body 228 and the front plate 230 via operation of the motor 212 and movement of the actuator plunger 213 and force gauge holder 225.

Referring to FIG. 2B, the actuator mechanism 210 is in an 'extended' position with the force gauge 220 moved forward through the front plate 230 of the machine system such that the contact end 220' of the force gauge 220 extends distally, with respect to the actuator mechanism 210, beyond the outer surface 230' of the front plate 230. The diaphragm 218 has been pushed into the fluid pathway 250 through physical contact with the contact end 220' of the force gauge 220. In accordance with various embodiments of the present specification, based on feedback provided to the controller by the force gauge, the controller has instructed the motor 212 to move the actuator plunger 213 to extend the force gauge holder 225 and force gauge 220 such that the contact end 220' of the force gauge 220 has come into contact with, and pushed forward, the diaphragm 218. The diaphragm 218 is extended into the fluid pathway 250 and is in contact with the valve seat 255, effectively closing the valve 261 and shutting off fluid flow. The gap at valve seat 255, as seen as gap 258 in FIG. 2A, has been closed in FIG. 2B. Pressure 270 increases around the diaphragm 218 and valve seat 255 and pushes against the diaphragm 218.

Figure 3A:
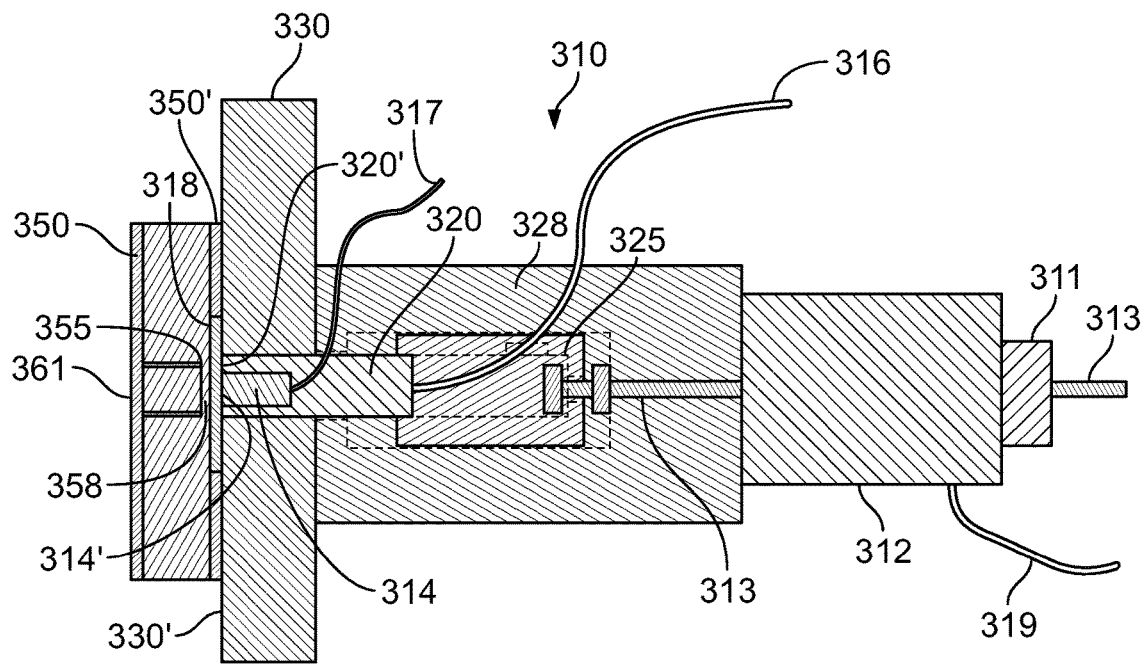
FIG. 3A is an illustration of an actuator mechanism with feedback control, comprising a pressure transducer and a force gauge, and an open valve of a fluid circuit, in accordance with one embodiment of the present specification.
Figure 3B:
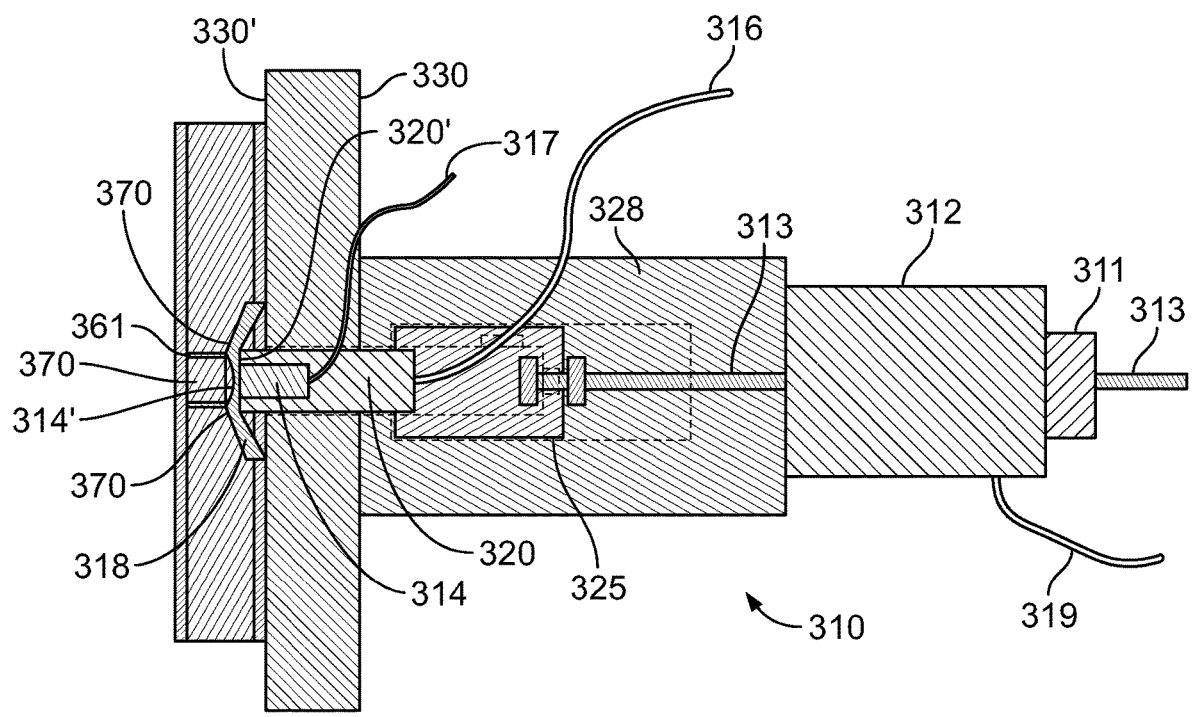
FIG. 3B is an illustration of an actuator mechanism with feedback control, comprising a pressure transducer and a force gauge, and a closed valve of a fluid circuit, in accordance with one embodiment of the present specification.

FIGS. 3A and 3B are illustrations of an actuator mechanism 310 with feedback control, comprising both a pressure transducer 314 and a force gauge 320, and an open valve and a closed valve, respectively, of a fluid circuit, in accordance with one embodiment of the present specification. Referring to both FIGS. 3A and 3B simultaneously, each actuator mechanism 310 includes an encoder 311, a stepper or DC linear actuator motor 312, an actuator plunger 313, an actuator mechanism body 328, a pressure transducer 314, a force gauge 320, and a pressure transducer/force gauge holder 325. A first signal wire 317 connects the pressure transducer 314 to a controller (not shown). A second signal wire 316 connects the force gauge 320 to a controller. A power and signal wire 319 connects the motor 312 to the controller. The encoder 311 acts to notify the system that the actuator mechanism is moving.

Referring to FIG. 3A, the actuator (pressure transducer 314 and force gauge 320 in this embodiment) is in its 'home' position within the front plate 330 of a machine system. The pressure transducer 314 and force gauge 320 function together as a linear member contained within a conduit (in this embodiment, a front plate 330 of a machine system) through which they extend axially. In one embodiment, the pressure transducer 314 and force gauge 320 are configured to sit adjacent one another within the front plate 330. In another embodiment, the pressure transducer 314 and force gauge 320 are configured to sit coaxially, one within the other, within the front plate 330. Specifically, when the actuator is in its 'home' position, the pressure transducer 314 and force gauge 320 of the actuator mechanism 310 rest embedded within the front plate 330 of a machine system, such as, in one embodiment, a portion of a dialysis system housing. In one embodiment, when the actuator is in the 'home' position, the pressure transducer 314 and force gauge 320 rest within the front plate 330 such that the contact end 314' of the pressure transducer 314 and the contact end 320' of the force gauge 320 are positioned just proximal to, with respect to the actuator mechanism 310, an outer surface 330' of the front plate 330. In other words, when the actuator is in the 'home' position, the contact end 314' of the pressure transducer 314 and the contact end 320' of the force gauge 320 are slightly recessed within the front plate 130. The contact ends 314', 320' are flush with one another. The pressure transducer 314 and force gauge 320 are linearly movable within the front plate 330 by activation of the motor 312 and linear movement of the actuator plunger 313 and pressure transducer/force gauge holder 325. The pressure transducer 314 and force gauge 320 can be moved forward, with respect to the actuator mechanism 310, such that their contact ends 314', 320' extend in unison beyond the outer surface 330' of the front plate 330. A fluid pathway 350 is positioned proximate, or adjacent to, the front plate 330. A diaphragm 318 is positioned in an outer wall 350' of the fluid pathway 350. In one embodiment, the outer wall 350' of the fluid pathway 350 is positioned proximate and adjacent to the outer surface 330' of the front plate 330 such that the diaphragm 318 is proximate to, and in linear alignment with, the pressure transducer 314 and force gauge 320 of the actuator mechanism 310. Since the actuator mechanism 310 is in the 'home' state, the diaphragm 318 is flat and is not in contact with either the pressure transducer 314 or the force gauge 320, and the valve is in the open state. Within the fluid pathway 350, a gap 358 at the valve 361 is present between the diaphragm 318 and valve seat 355, allowing fluid to flow through.

In one embodiment, referring to FIG. 3A, the components of the actuator mechanism 310 are arranged in the following configuration. As mentioned above, in one embodiment, the pressure transducer 314 and force gauge 320 function together as the actuator. The pressure transducer 314 and force gauge 320, pressure transducer/force gauge holder 325, and actuator plunger 313 are linearly movable as a unit via operation of the motor 312 and extend axially throughout the actuator mechanism 310. Using the diaphragm 318 of the outer wall 350' of the fluid pathway 350 as a reference point, the encoder 311 comprises the distal endpoint of the actuator mechanism 310. In one embodiment, a portion of the actuator plunger 313 extends distally from the distal end of the encoder 311. During operation, as the motor 312 moves the actuator plunger 313 toward the diaphragm 318, the portion of the plunger 313 extending from the distal end of the encoder 311 moves proximally through said encoder 311.

Next to the encoder 311 and at a position more proximal to the diaphragm 318 is the motor 312. The plunger 313 extends axially through the motor 312. Positioned proximal to the motor 312 is the actuator mechanism body 328. The distal end of the actuator mechanism body 328 is positioned adjacent to motor 312 and the proximal end of the actuator mechanism 328 is positioned adjacent to the front plate 330 of the machine system. A proximal portion of the actuator plunger 313 extends through the distal portion of the actuator mechanism body 328. Attached to the proximal end of the actuator plunger 313 and housed within the actuator mechanism body 328 is the pressure transducer/force gauge holder 325. Through action of the motor 312 and extension/retraction of the actuator plunger 313, the pressure transducer/force gauge holder 325 is linearly movable within the actuator mechanism body 328. Attached to a proximal end of the pressure transducer/force gauge holder 325 are the pressure transducer 314 and force gauge 320. The pressure transducer 314 and force gauge 320 extend axially partially through the actuator mechanism body 328 and partially through the front plate 330. The pressure transducer 314 and force gauge 320 are linearly movable within the proximal portion of the actuator mechanism body 328 and the front plate 330 via operation of the motor 312 and movement of the actuator plunger 313 and pressure transducer/force gauge holder 325.

Referring to FIG. 3B, the actuator mechanism 310 is in an 'extended' position with the pressure transducer 314 and force gauge 320 moved forward through the front plate 330 of the machine system such that the contact end 314' of the pressure transducer 114 and the contact end of the force gauge 320' extend distally, with respect to the actuator mechanism 310, beyond the outer surface 330' of the front plate 330. The diaphragm 318 has been pushed into the fluid pathway 350 through physical contact with both the contact end 314' of the pressure transducer 314 and the contact end 320' of the force gauge 320. In accordance with various embodiments of the present specification, based on feedback provided to the controller by the pressure transducer 314 and force gauge 320, the controller has instructed the motor 312 to move the actuator plunger 313 to extend the pressure transducer/force gauge holder 325, pressure transducer 314, and force gauge 320, such that both the contact end 314' of the pressure transducer 314 and the contact end 320' of the force gauge 320 have come into contact with, and pushed forward, the diaphragm 318. The diaphragm 318 is extended into the fluid pathway 350 and is in contact with the valve seat 355, effectively closing the valve 361 and shutting off fluid flow. The gap at valve seat 355, as seen as gap 358 in FIG. 3A, has been closed in FIG. 3B. Pressure 370 increases around the diaphragm 318 and valve seat 355 and pushes against the diaphragm 318.

In the above embodiments, as the diaphragm begins to thin or soften due to temperature changes or other effects, the pressure transducer will sense a decrease in pressure and/or the force gauge will sense a decrease in force at the contact end of the actuator. This decrease in pressure and/or force will translate to a decrease in positive voltage which will be relayed to the controller. The controller will then instruct the actuator to extend further until the voltage values once again match the known closure values, signifying that the weakened diaphragm has been pushed further onto the valve seat to ensure complete valve closure.

Figure 4A:
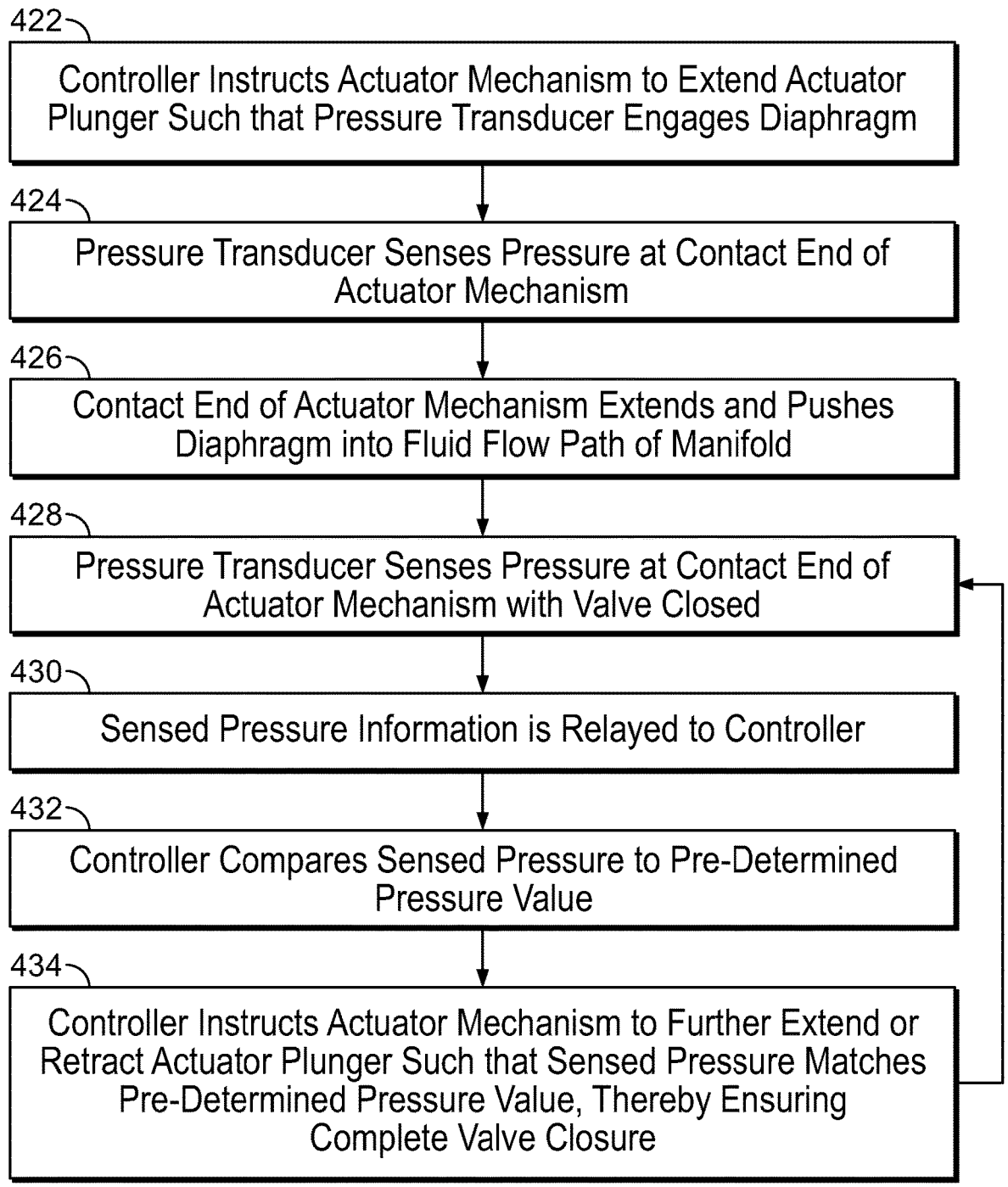
FIG. 4A is a flow chart illustrating the steps involved in achieving a valve close state of a fluid circuit using an actuator mechanism with feedback control, comprising a pressure transducer, as described with reference to FIGS. 1A and 1B.

FIG. 4A is a flow chart illustrating the steps involved in achieving a valve close state of a fluid circuit using an actuator mechanism with feedback control, comprising a pressure transducer, as described with reference to FIGS. 1A and 1B. At step 422, the controller instructs the actuator mechanism to extend the actuator plunger such that the pressure transducer on the contact end of the actuator mechanism engages the diaphragm. Optionally, at step 424, the pressure transducer senses pressure applied by the diaphragm against the pressure transducer. Then, at step 426, the controller instructs the actuator mechanism to close the valve by further extending the contact end of the actuator mechanism to push the diaphragm into the flow path of the fluid circuit. The pressure transducer then senses the pressure applied against the transducer by the diaphragm while the valve is in a closed state at step 428. The sensed pressure is relayed to the controller at step 430. At step 432, the controller compares the sensed pressure value to a pre-determined pressure value. The controller then instructs the actuator mechanism to further extend or retract the actuator plunger at step 434 such that the sensed pressure matches the pre-determined pressure value, thereby ensuring complete valve closure. The pressure is continually sensed at step 428 so that fine tune adjustments to the actuator position can be made in real-time to maintain the valve in a close state.

Figure 4B:
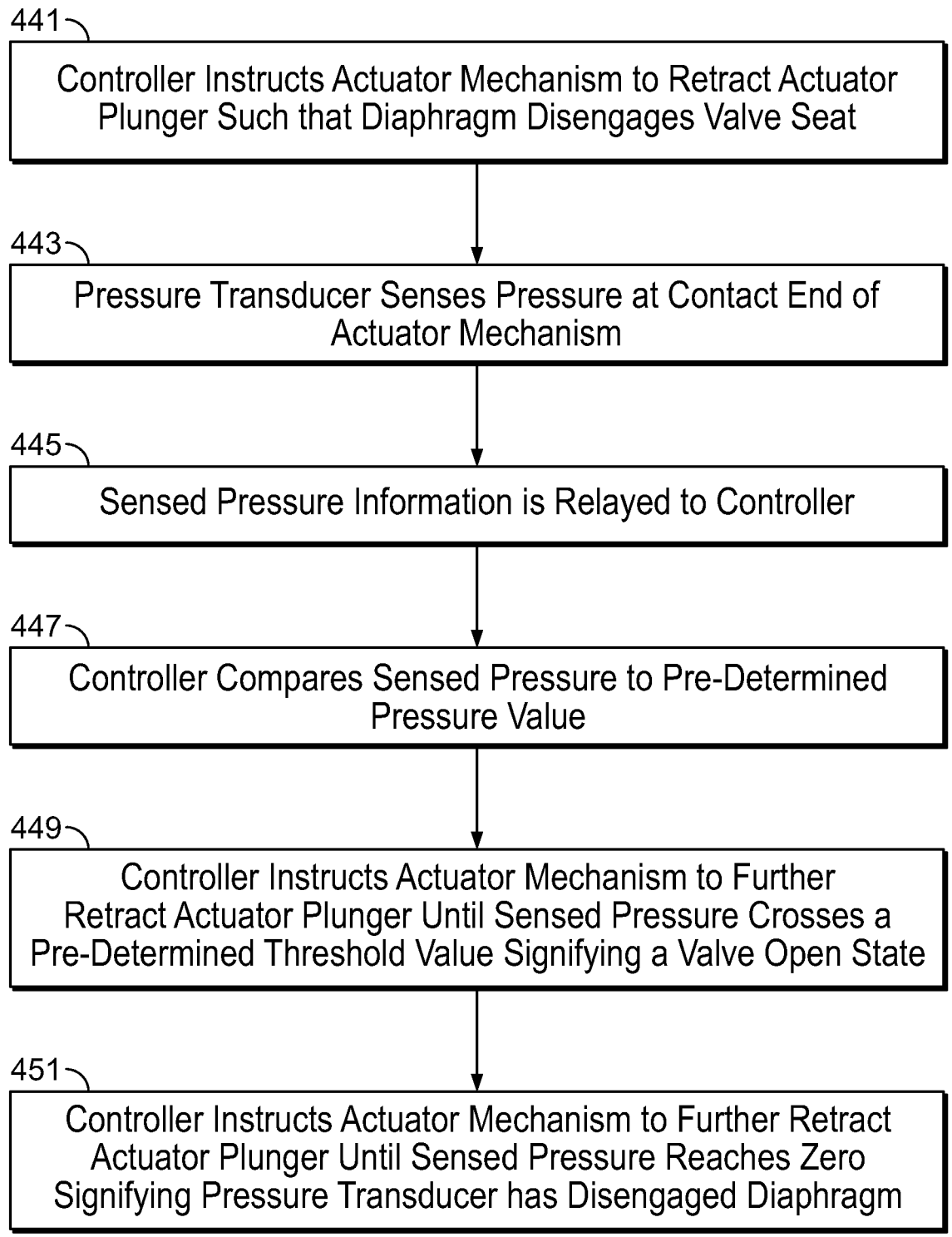
FIG. 4B is a flow chart illustrating the steps involved in achieving a valve open state of a fluid circuit using an actuator mechanism with feedback control, comprising a pressure transducer, as described with reference to FIGS. 1A and 1B.

FIG. 4B is a flow chart illustrating the steps involved in achieving a valve open state of a fluid circuit using an actuator mechanism with feedback control, comprising a pressure transducer, as described with reference to FIGS. 1A and 1B. At step 441, while the valve is in a closed state, the controller instructs the actuator mechanism to retract the actuator plunger such that the diaphragm disengages the valve seat. The pressure transducer then senses the pressure applied against the transducer by the diaphragm at step 443. The sensed pressure is relayed to the controller at step 445. At step 447, the controller compares the sensed pressure value to a pre-determined pressure value. The controller then instructs the actuator mechanism to further retract the actuator plunger at step 449 such that the sensed pressure crosses a pre-determined threshold value, signifying a valve open state has been achieved. Optionally, in one embodiment, the controller instructs the actuator mechanism to further retract the actuator plunger at step 451 until the sensed pressure reaches zero, signifying that the pressure transducer has disengaged the diaphragm, the diaphragm is in a relaxed configuration, and the valve is completely open.

Figure 5A:
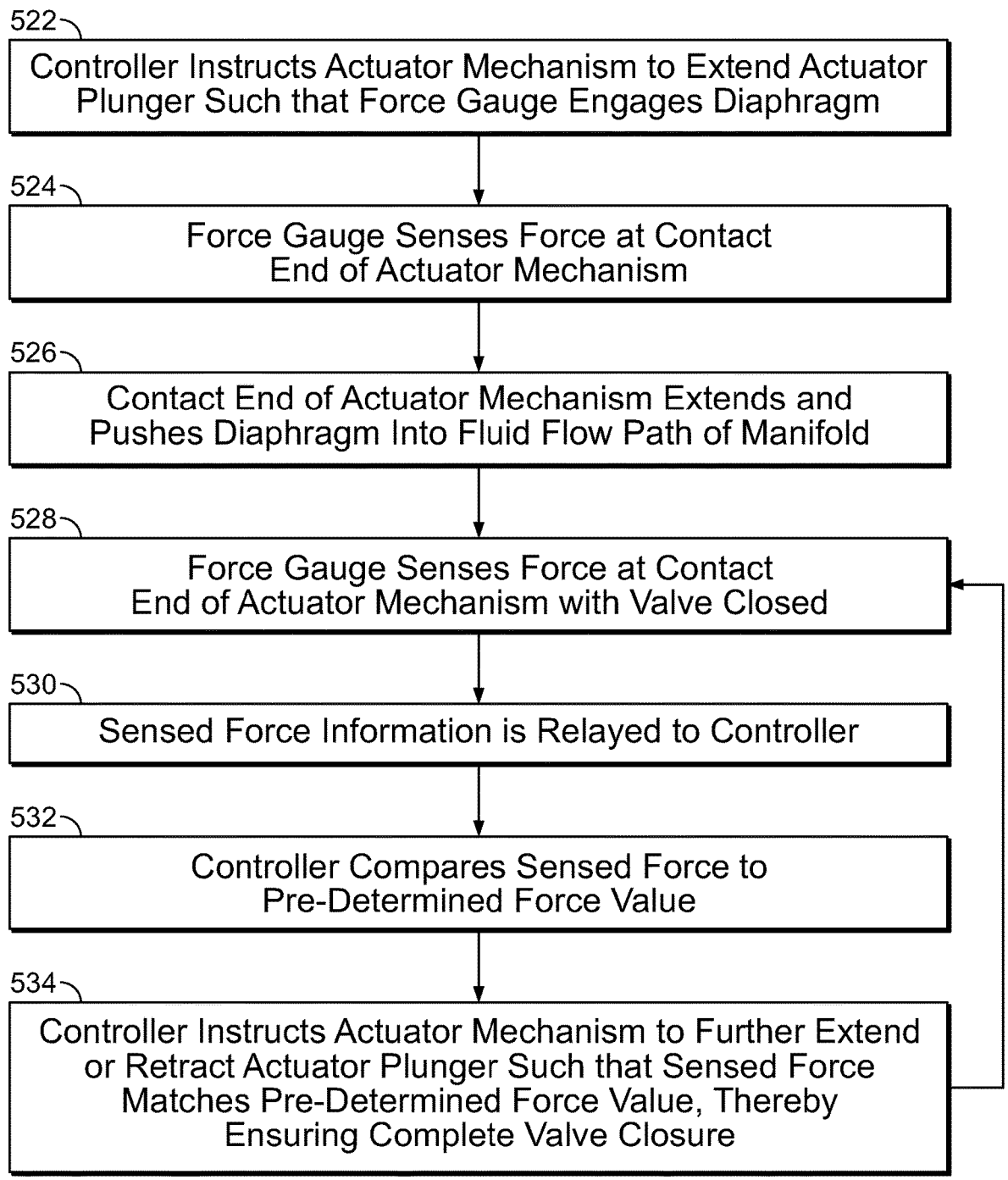
FIG. 5A is a flow chart illustrating the steps involved in achieving a valve close state of a fluid circuit using an actuator mechanism with feedback control, comprising a force gauge, as described with reference to FIGS. 2A and 2B.

FIG. 5A is a flow chart illustrating the steps involved in achieving a valve close state of a fluid circuit using an actuator mechanism with feedback control, comprising a force gauge, as described with reference to FIGS. 2A and 2B. At step 522, the controller instructs the actuator mechanism to extend the actuator plunger such that the force gauge on the contact end of the actuator mechanism engages the diaphragm. Optionally, at step 524, the force gauge senses force applied by the diaphragm against the force gauge. Then, at step 526, the controller instructs the actuator mechanism to close the valve by further extending the contact end of the actuator mechanism to push the diaphragm into the flow path of the fluid circuit. The force gauge then senses the force applied against the gauge by the diaphragm while the valve is in a closed state at step 528. The sensed force is relayed to the controller at step 530. At step 532, the controller compares the sensed force value to a pre-determined force value. The controller then instructs the actuator mechanism to further extend or retract the actuator plunger at step 534 such that the sensed force matches the pre-determined force value, thereby ensuring complete valve closure. The force is continually sensed at step 528 so that fine tune adjustments to the actuator position can be made in real-time to maintain the valve in a close state.

Figure 5B:
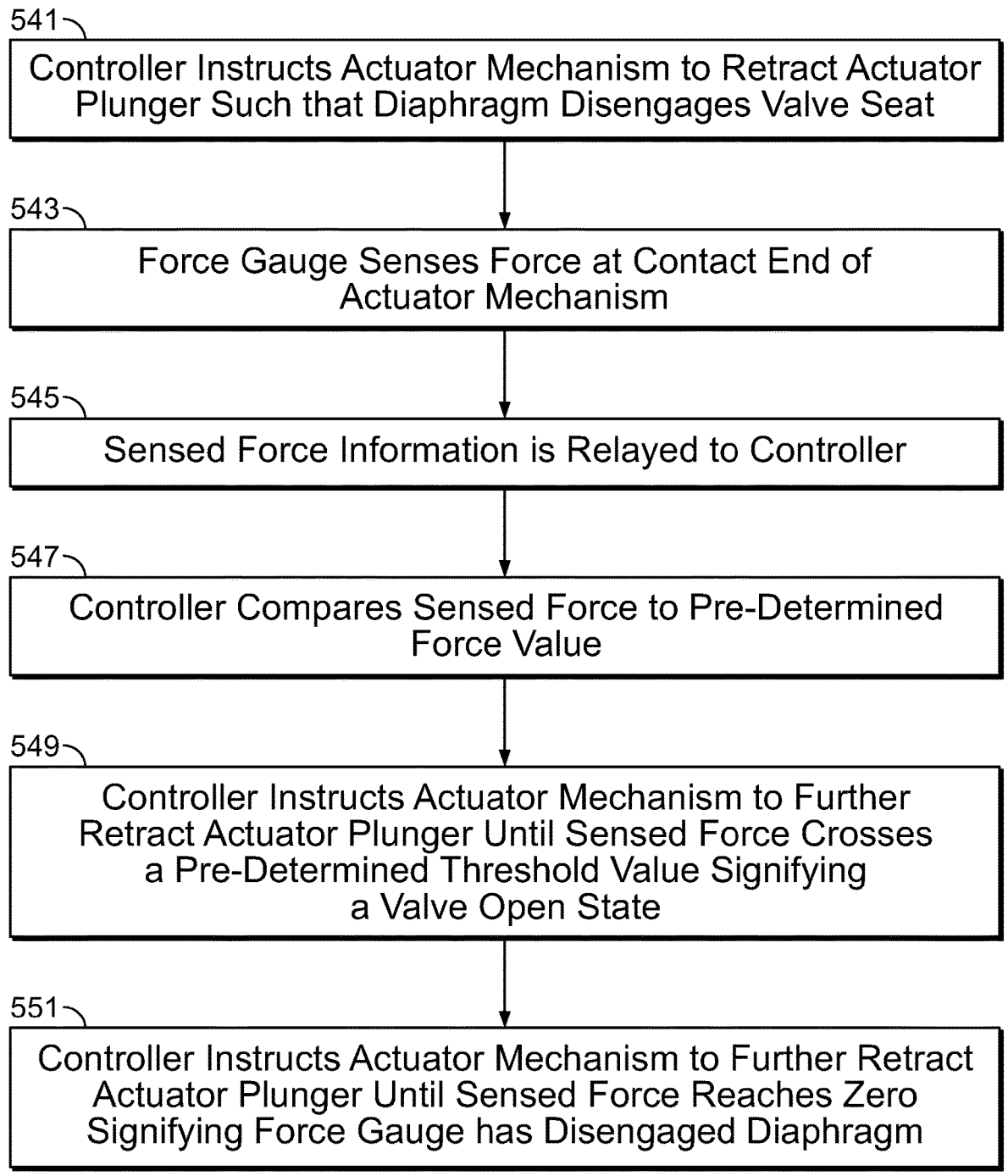
FIG. 5B is a flow chart illustrating the steps involved in achieving a valve open state of a fluid circuit using an actuator mechanism with feedback control, comprising a force gauge, as described with reference to FIGS. 2A and 2B.

FIG. 5B is a flow chart illustrating the steps involved in achieving a valve open state of a fluid circuit using an actuator mechanism with feedback control, comprising a force gauge, as described with reference to FIGS. 2A and 2B. At step 541, while the valve is in a closed state, the controller instructs the actuator mechanism to retract the actuator plunger such that the diaphragm disengages the valve seat. The force gauge then senses the force applied to the gauge by the diaphragm at step 543. The sensed force is relayed to the controller at step 545. At step 547, the controller compares the sensed force value to a pre-determined force value. The controller then instructs the actuator mechanism to further retract the actuator plunger at step 549 such that the sensed force crosses a pre-determined threshold value, signifying a valve open state has been achieved. Optionally, in one embodiment, the controller instructs the actuator mechanism to further retract the actuator plunger at step 551 until the sensed force reaches zero, signifying that the force gauge has disengaged the diaphragm, the diaphragm is in a relaxed configuration, and the valve is completely open.

Figure 6A:
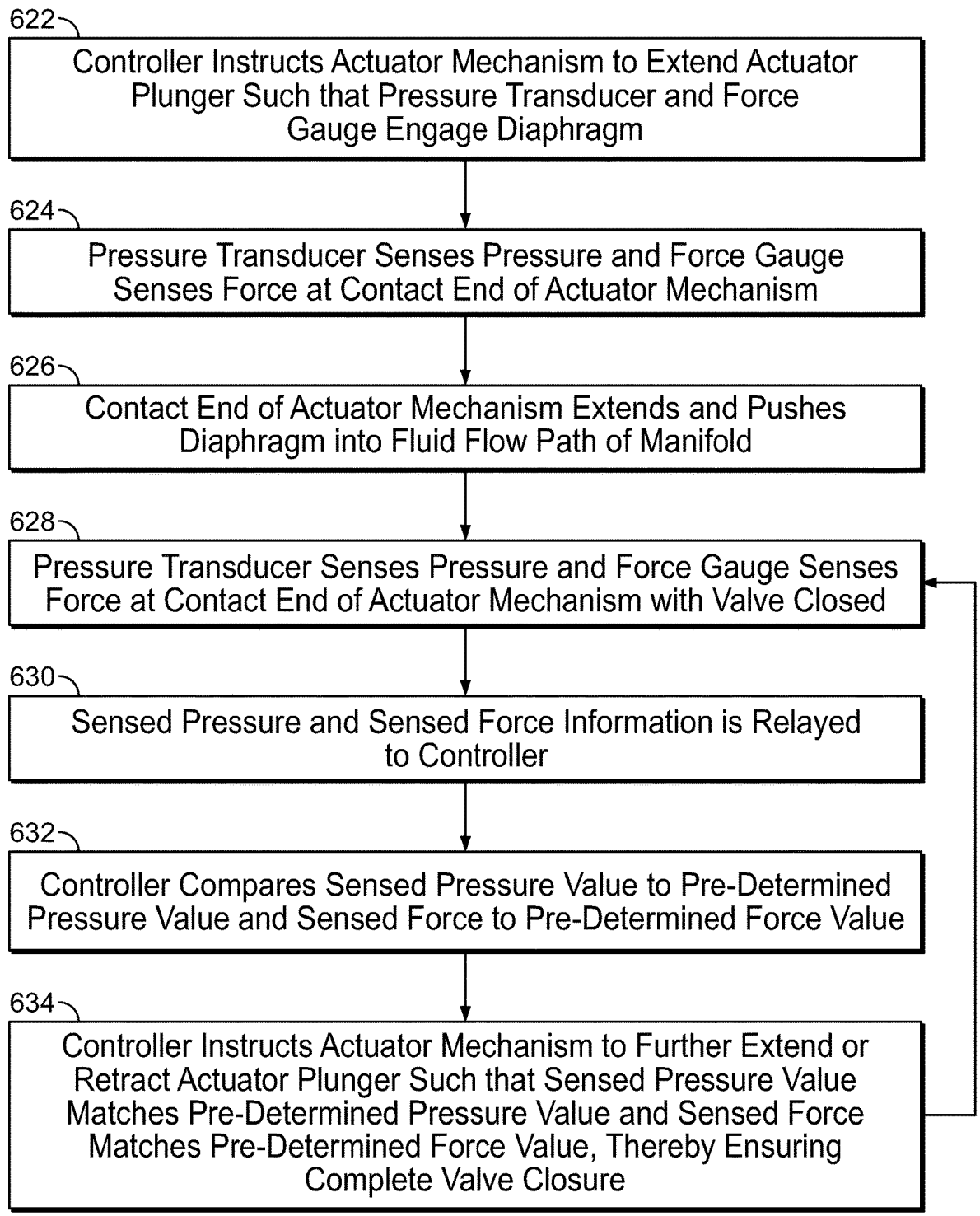
FIG. 6A is a flow chart illustrating the steps involved in achieving a valve close state of a fluid circuit using an actuator mechanism with feedback control, comprising a pressure transducer and a force gauge, as described with reference to FIGS. 3A and 3B; and, FIG. 6B is a flow chart illustrating the steps involved in achieving a valve open state of a fluid circuit using an actuator mechanism with feedback control, comprising a pressure transducer and a force gauge, as described with reference to FIGS. 3A and 3B.

FIG. 6 is a flow chart illustrating the steps involved in achieving a valve close state of a fluid circuit using an actuator mechanism with feedback control, comprising a pressure transducer and a force gauge, as described with reference to FIGS. 3A and 3B. At step 622, the controller instructs the actuator mechanism to extend the actuator plunger such that the pressure transducer and the force gauge on the contact end of the actuator mechanism engage the diaphragm. Optionally, at step 624, the pressure transducer senses the pressure applied by the diaphragm against the pressure transducer and the force gauge senses the force applied by the diaphragm against the force gauge. Then, at step 626, the controller instructs the actuator mechanism to close the valve by further extending the contact end of the actuator mechanism to push the diaphragm into the flow path of the fluid circuit. The pressure transducer then senses the pressure applied against the transducer by the diaphragm and the force gauge then senses the force applied against the gauge by the diaphragm while the valve is in a closed state at step 628. The sensed pressure and sensed force are relayed to the controller at step 630. At step 632, the controller compares the sensed pressure value to a pre-determined pressure value and the sensed force value to a pre-determined force value. The controller then instructs the actuator mechanism to further extend or retract the actuator plunger at step 634 such that the sensed pressure matches the pre-determined pressure value and the sensed force matches the pre-determined force value, thereby ensuring complete valve closure. The pressure and force are continually sensed at step 628 so that fine tune adjustments to the actuator position can be made in real-time to maintain the valve in a close state.

Figure 6B:
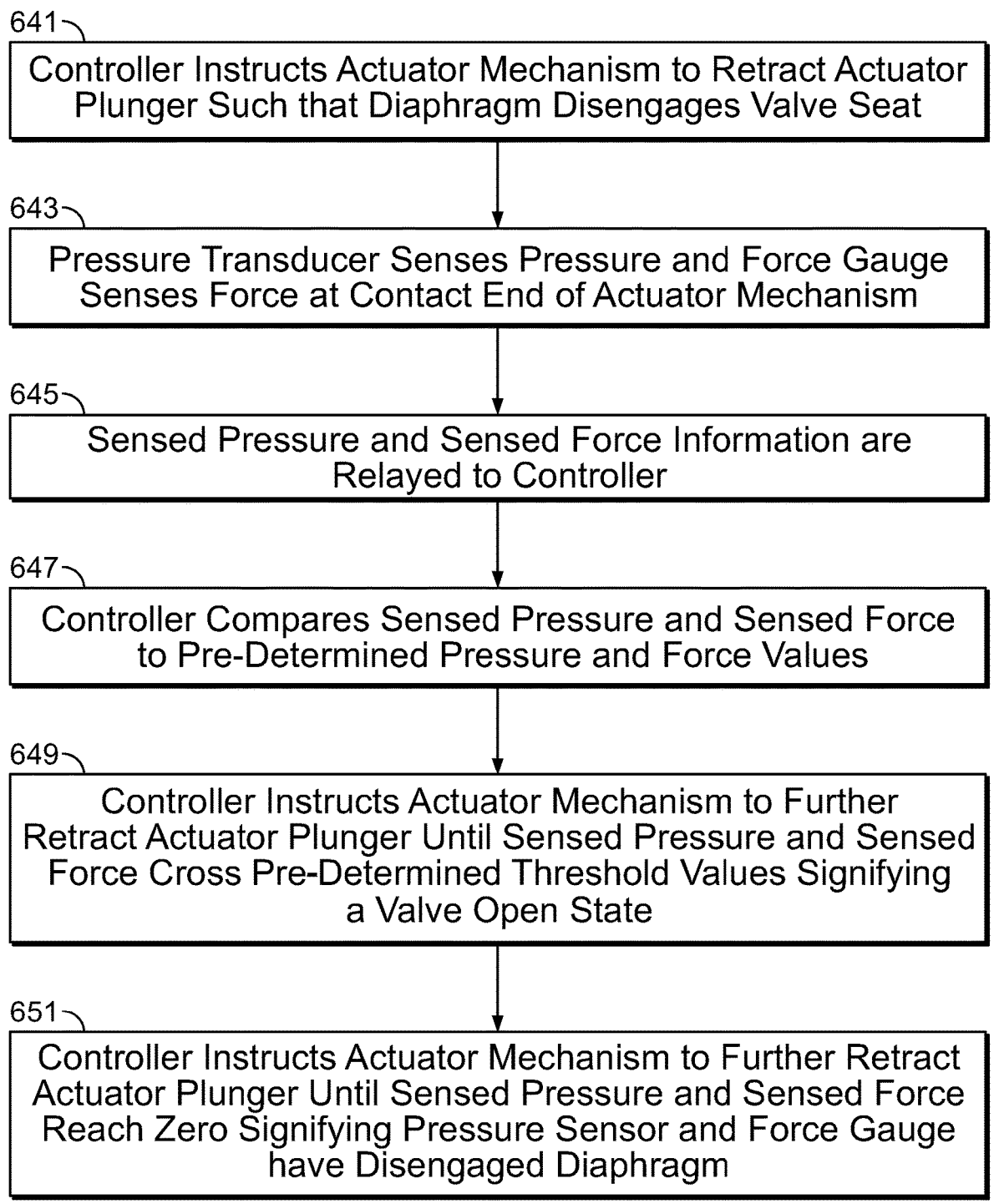

FIG. 6B is a flow chart illustrating the steps involved in achieving a valve open state of a fluid circuit using an actuator mechanism with feedback control, comprising a pressure transducer and a force gauge, as described with reference to FIGS. 3A and 3B. At step 641, while the valve is in a closed state, the controller instructs the actuator mechanism to retract the actuator plunger such that the diaphragm disengages the valve seat. The pressure transducer and force gauge then sense the pressure and force respectively, applied against the transducer by the diaphragm at step 643. The sensed pressure and force are relayed to the controller at step 645. At step 647, the controller compares the sensed pressure value and sensed pressure value to pre-determined pressure and force values. The controller then instructs the actuator mechanism to further retract the actuator plunger at step 649 such that the sensed pressure and force cross pre-determined threshold values, signifying a valve open state has been achieved. Optionally, in one embodiment, the controller instructs the actuator mechanism to further retract the actuator plunger at step 651 until the sensed pressure and sensed force both reach zero, signifying that the pressure transducer and force gauge have disengaged the diaphragm, the diaphragm is in a relaxed configuration, and the valve is completely open.

As discussed earlier, the actuator mechanism of the present specification can be used in a variety of applications having a membrane or diaphragm type valve in a fluid circuit. In various embodiments, depending upon the application, the actuator mechanism can be configured to move the actuator to maintain the pressure or force within any range or at any value as sensed by the pressure transducer or force gauge respectively, to keep the valve closed.

For example, in one embodiment, the actuator mechanism of the present specification can be used in a portable kidney dialysis system having a disposable manifold for fluidic circuits. One of ordinary skill in the art would appreciate that the actuator mechanism with feedback control system could be implemented with a disposable manifold by positioning the actuator external to the manifold at the desired valve location. This type of actuator is also separate and distinct from the disposable manifold and generally part of the non-disposable portion of the kidney dialysis system. Valve systems are preferably implemented in a disposable type of manifold using elastic membranes at flow control points which are selectively occluded, as required, by protrusions, pins, or other members extending from the machine. In various embodiments, fluid occlusion is enabled using an on/off DC motor, a stepper motor controlled by a controller, or a safe, low-energy magnetic valve. In one embodiment, the valve system is similar to that disclosed in U.S. patent application Ser. No. 13/023,490, assigned to the applicant of the present invention, filed on Feb. 8, 2011, and entitled "Portable Dialysis Machine", which is hereby incorporated by reference in its entirety. In another embodiment, the valve system is similar to that disclosed in U.S. patent application Ser. No. 13/726,457, assigned to the applicant of the present invention, filed on Dec. 24, 2012, and entitled "Portable Dialysis Machine with Improved Reservoir Heating System", which is hereby incorporated by reference in its entirety. In one embodiment, a valve actuator mechanism having a pressure transducer as disclosed in the present specification is used in a dialysis machine to maintain a sensed pressure of at least 2 psi, ensuring valve closure. In another embodiment, a valve actuator mechanism having a force gauge as disclosed in the present specification is used in a dialysis machine to maintain a sensed force of at least 5 pound-force ($lb_F$), ensuring valve closure. In yet another embodiment, a valve actuator mechanism having both a pressure transducer and a force gauge as disclosed in the present specification is used in a dialysis machine to maintain a sensed pressure of at least 2 psi and a sensed force of at least 5 pound-force ($lb_F$), ensuring valve closure.

In one embodiment, the diaphragms used as valves are similar to those described in the '490 application referenced above. In another embodiment, the diaphragms used as valves are similar to those disclosed in U.S. patent application Ser. No. 13/852,918, assigned to the applicant of the present invention, filed on Mar. 28, 2013, and entitled "Manifold Diaphragms", which is hereby incorporated by reference in its entirety.

In general, the actuator mechanism with feedback control of the present specification can be used with a valve in a kidney dialysis system having the following attributes: a) two stable states, open and closed, b) changing states requires energy input, c) maintaining a state does not require energy input, d) a state is changed by the use of electronic forces to modify the position of a displacement member which, when modified, causes a valve to either open or close.

The above examples are merely illustrative of the many applications of the system of the present invention. Although only a few embodiments of the present invention have been described herein, it should be understood that the present invention might be embodied in many other specific forms without departing from the spirit or scope of the invention. Therefore, the present examples and embodiments are to be considered as illustrative and not restrictive, and the invention may be modified within the scope of the appended claims.

I claim:

1. A valve actuator system adapted to open and close a valve, comprising an orifice closing member adjacent a fluid pathway through which fluid flows in a dialysis system, the valve actuator mechanism comprising:

a displacement system, wherein the displacement system comprises a displacement member adapted to being displaced linearly and having a contact end positioned proximate to the orifice closing member when the valve is in the open state, and wherein the displacement system comprises at least one pressure sensor configured to sense pressure generated when the contact end is in physical communication with the orifice closing member and to relay data based on the sensed pressure;

a mechanism for moving the displacement member; and a controller configured to receive the sensed pressure from the at least one pressure sensor, wherein the controller comprises a memory having stored therein a plurality of programmatic instructions that, when executed by a processing unit, compare the sensed pressure to a pre-determined value stored in the memory and activate the mechanism to move the displacement member toward or away from the orifice closing member to optimally position the contact end against the orifice closing member such that the mechanism maintains a sensed pressure of at least 2 psi.

2. The valve actuator system of claim 1, wherein the mechanism comprises a stepper motor.

3. The valve actuator system of claim 1, wherein the mechanism comprises a DC motor.

4. The valve actuator system of claim 1, further comprising an encoder for determining an amount of movement of the displacement member.

5. The valve actuator system of claim 1 for use in a dialysis machine.

6. A valve actuator system adapted to open and close a valve, comprising an orifice closing member adjacent a fluid pathway through which fluid flows in a dialysis system, the valve actuator mechanism comprising:

a displacement system, wherein the displacement system comprises a displacement member adapted to being displaced linearly and having a contact end positioned proximate to the orifice closing member when the valve is in the open state, and wherein the displacement system comprises at least one force sensor configured to sense force generated when the contact end is in physical communication with the orifice closing member and to relay data based on the sensed force;

a mechanism for moving the displacement member; and a controller adapted to receive the sensed force from the at least one force sensor, wherein the controller comprises a memory having stored therein a plurality of programmatic instructions that, when executed by a processing unit, compare the sensed force to a pre-determined value stored in the memory and activate the mechanism to move the displacement member toward or away from the orifice closing member to optimally position the contact end against the orifice closing member such that the mechanism maintains a force of at least 5 pound-force.

7. The valve actuator system of claim 6, wherein the mechanism comprises a stepper motor.

8. The valve actuator system of claim 6, wherein the mechanism comprises a DC motor.

9. The valve actuator system of claim 6, further comprising an encoder for determining an amount of movement of the displacement member.

10. The valve actuator system of claim 6 for use in a dialysis machine.

11. A valve actuator system adapted to open and close a valve, comprising an orifice closing member and adjacent a fluid pathway through which fluid flows in a dialysis system, the valve actuator mechanism comprising:
   a displacement system, wherein the displacement system comprises a displacement member adapted to being displaced linearly and having a contact end wherein the contact end is positioned proximate to the orifice closing member when the valve is in the open state, wherein the displacement system comprises at least one pressure sensor, configured to sense pressure generated when the contact end is in physical communication with the orifice closing member and to relay data based on the sensed pressure, and wherein the displacement system comprises at least one force gauge configured to sense a force generated when the contact end is in physical communication with the orifice closing member and to relay data based on the sensed force;
   a mechanism for moving the displacement member; and
   a controller configured to receive the sensed pressure from the at least one pressure sensor and the sensed force from the at least one force gauge, wherein the controller comprises a memory having stored therein a plurality of programmatic instructions that, when executed by a processing unit, compares the sensed pressure to a pre-determined pressure value stored in the memory and the sensed force to a pre-determined force value stored is the memory and activate the mechanism to move the displacement member toward or away from the orifice closing member to optimally position the contact end against the orifice closing member such that the mechanism maintains a sensed pressure of at least 2 psi and a force of at least 5 pound-force.

12. The valve actuator system of claim 11, wherein the mechanism comprises a stepper motor.

13. The valve actuator system of claim 11, wherein the mechanism comprises a DC motor.

14. The valve actuator system of claim 11, further comprising an encoder for determining an amount of movement of the displacement member.

15. The valve actuator system of claim 11 for use in a dialysis machine.

* * * * *